US012279949B2

(12) United States Patent
Vidlund

(10) Patent No.: US 12,279,949 B2
(45) Date of Patent: Apr. 22, 2025

(54) CONTROLLED EXPRESSION OF EXPANDABLE HEART VALVE

(71) Applicant: Cephea Valve Technologies, Inc., Santa Clara, CA (US)

(72) Inventor: Zachary R. Vidlund, Robbinsdale, MN (US)

(73) Assignee: Cephea Valve Technologies, Inc., Abbott Park, IL (US)

(*) Notice: Subject to any disclaimer, the term of this patent is extended or adjusted under 35 U.S.C. 154(b) by 145 days.

(21) Appl. No.: 17/400,184

(22) Filed: Aug. 12, 2021

(65) Prior Publication Data
US 2022/0087814 A1 Mar. 24, 2022

Related U.S. Application Data

(60) Provisional application No. 63/082,493, filed on Sep. 24, 2020.

(51) Int. Cl.
A61F 2/24 (2006.01)
(52) U.S. Cl.
CPC .......... *A61F 2/2409* (2013.01); *A61F 2/2436* (2013.01); *A61F 2210/0014* (2013.01)
(58) Field of Classification Search
CPC .......... A61F 2/2418; A61F 2002/30706; A61F 2250/0048; A61F 2220/0075
See application file for complete search history.

(56) References Cited

U.S. PATENT DOCUMENTS 6,821,297 B2 11/2004 Snyders
7,947,075 B2 5/2011 Goetz et al.
8,652,203 B2 2/2014 Quadri et al.
8,845,720 B2 9/2014 Conklin
9,655,722 B2 5/2017 Morriss et al.
9,730,790 B2 8/2017 Quadri et al.
(Continued)

FOREIGN PATENT DOCUMENTS

WO 2012177942 A2 12/2012
WO 2013059747 4/2013
(Continued)

OTHER PUBLICATIONS

Britannica, The Editors of Encyclopaedia. "polyethylene terephthalate". Encyclopedia Britannica, Sep. 23, 2022, https://www.britannica.com/science/polyethylene-terephthalate. (Year: 2022).*

Primary Examiner — Javier G Blanco
(74) Attorney, Agent, or Firm — SLEMAN & LUND LLP

(57) ABSTRACT

A prosthetic heart valve includes a collapsible and expandable outer frame, a collapsible and expandable inner frame, and a prosthetic valve assembly. The outer frame may be configured to engage tissue of a native heart valve, and may have (i) an atrial portion adapted to be positioned on an atrial side of the native heart valve; (ii) a ventricle portion adapted to be positioned on a ventricle side of the native heart valve; and (iii) a narrowed waist portion between the atrial portion and the ventricle portion. The inner frame may be positioned radially inward of the outer frame and may be coupled to the outer frame. A constraining band may extend around a circumference of the inner frame. The prosthetic valve assembly may be coupled to, and positioned radially inward of, the inner frame.

17 Claims, 13 Drawing Sheets

(56) References Cited

U.S. PATENT DOCUMENTS

| | | |
|---|---|---|
| 10,016,271 B2 | 7/2018 | Morriss et al. |
| 10,080,653 B2 | 9/2018 | Conklin et al. |
| 10,172,710 B2 | 1/2019 | Drasler et al. |
| 10,232,564 B2 | 3/2019 | Pelled et al. |
| 10,363,130 B2 | 7/2019 | Armer et al. |
| 10,575,951 B2 | 3/2020 | Johnson et al. |
| 2002/0123802 A1* | 9/2002 | Snyders ............ A61F 2/2436 623/2.11 |
| 2010/0145438 A1* | 6/2010 | Barone ............ A61F 2/2418 623/2.38 |
| 2010/0256723 A1* | 10/2010 | Murray ............ A61F 2/2418 623/1.2 |
| 2011/0106120 A1* | 5/2011 | Haselby ............ A61M 60/178 606/153 |
| 2013/0144378 A1* | 6/2013 | Quadri ............ A61F 2/2418 623/2.1 |
| 2014/0121763 A1* | 5/2014 | Duffy ............ A61F 2/2412 623/2.11 |
| 2014/0194983 A1* | 7/2014 | Kovalsky ............ A61F 2/2418 623/2.38 |
| 2014/0277422 A1* | 9/2014 | Ratz ............ A61F 2/2418 623/2.37 |
| 2014/0277427 A1* | 9/2014 | Ratz ............ A61F 2/2409 623/2.38 |
| 2016/0262878 A1* | 9/2016 | Backus ............ A61F 2/2439 |
| 2018/0296341 A1 | 10/2018 | Noe et al. |
| 2018/0344457 A1 | 12/2018 | Gross |
| 2019/0069995 A1* | 3/2019 | Levi ............ A61F 2/2409 |
| 2019/0175338 A1* | 6/2019 | White ............ A61F 2/2409 |
| 2019/0209320 A1* | 7/2019 | Drasler ............ A61F 2/2433 |
| 2019/0321171 A1* | 10/2019 | Morriss ............ A61F 2/2436 |
| 2020/0069840 A1* | 3/2020 | Matheny ............ A61L 27/54 |
| 2020/0306040 A1 | 10/2020 | Fung et al. |
| 2023/0011247 A1* | 1/2023 | Zamani ............ A61F 2/2436 |

FOREIGN PATENT DOCUMENTS

| | | | |
|---|---|---|---|
| WO | 2018136959 A1 | 7/2018 | |
| WO | WO-2020117887 A1 * | 6/2020 | ......... A61F 2/2418 |

* cited by examiner

CONTROLLED EXPRESSION OF EXPANDABLE HEART VALVE

CROSS-REFERENCE TO RELATED APPLICATIONS

This application claims priority of the filing date of U.S. Provisional Patent Application No. 63/082,493, filed Sep. 24, 2020 and titled "Controlled Expression of Expandable Heart Valve," the disclosure of which is hereby incorporated by reference herein.

BACKGROUND OF THE DISCLOSURE

Heart valve disease is a significant cause of morbidity and mortality. A primary treatment of this disease is valve replacement. One form of replacement device is a bioprosthetic valve. Collapsing these valves to a smaller size or into a delivery system enables less invasive delivery approaches compared to conventional open-chest, open-heart surgery. Collapsing the implant to a smaller size and using a smaller delivery system minimizes the access site size and reduces the number of potential periprocedural complications.

When a self-expanding prosthetic heart valve is deployed into the native heart valve from a delivery device, the prosthetic heart valve will expand into the native valve annulus. Preferably, the way in which the prosthetic heart valve deploys (which may be referred to herein as "expression" of the prosthetic heart valve) is both controllable and has predictable and/or consistent results.

BRIEF SUMMARY OF THE DISCLOSURE

According to one aspect of the disclosure, a prosthetic heart valve includes a collapsible and expandable outer frame, a collapsible and expandable inner frame, and a prosthetic valve assembly. The outer frame may be configured to engage tissue of a native heart valve, and may have (i) an atrial portion adapted to be positioned on an atrial side of the native heart valve; (ii) a ventricle portion adapted to be positioned on a ventricle side of the native heart valve; and (iii) a narrowed waist portion between the atrial portion and the ventricle portion. The inner frame may be positioned radially inward of the outer frame and may be coupled to the outer frame. A constraining band may extend around a circumference of the inner frame. The prosthetic valve assembly may be coupled to, and positioned radially inward of, the inner frame.

According to another aspect of the disclosure, a method of implanting a prosthetic heart valve into a native heart valve annulus includes delivering the prosthetic heart valve to a location at or adjacent the native heart valve annulus while the prosthetic heart valve is maintained in a collapsed condition within an overlying sheath of a delivery device. The prosthetic heart valve may include a collapsible and expandable outer frame, a collapsible and expandable inner frame positioned radially inward of the outer frame and coupled to the outer frame, a prosthetic valve assembly coupled to, and positioned radially inward of, the inner frame, and a constraining band extending around a circumference of the inner frame. The method may also include deploying an outflow end of the prosthetic heart valve from the delivery device, and deploying an inflow end of the prosthetic heart valve from the delivery device after deploying the outflow end of the prosthetic heart valve, so that the inner frame has a first diameter after deployment of the inflow end of the prosthetic heart valve. The constraining band may prevent the inner frame from expanding to a second diameter larger than the first diameter during deployment of the outflow end of the prosthetic heart valve.

DETAILED DESCRIPTION

Figure 1A:
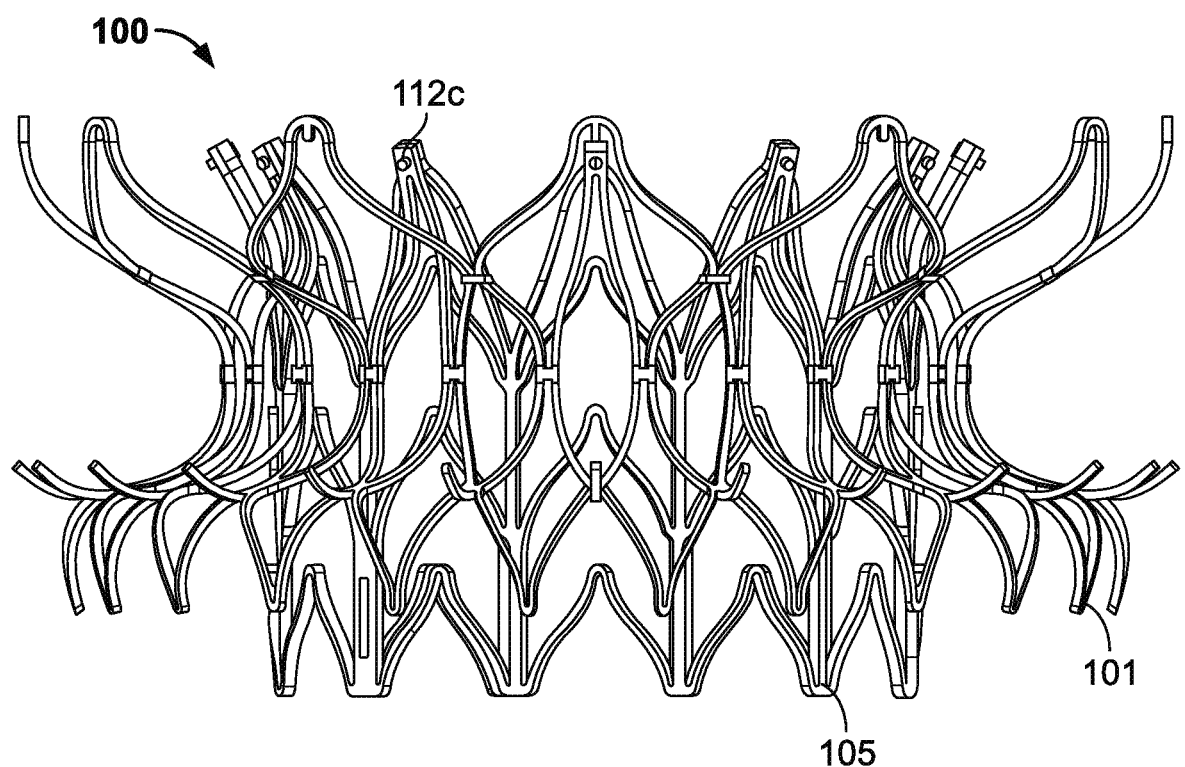
FIG. 1A is a perspective view of an assembled stent frame of a prosthetic heart valve of the prior art, the stent frame being shown in an expanded condition.

As used herein, the term "inflow end," when used in connection with a prosthetic heart valve, refers to an end of the prosthetic heart valve into which blood first flows when the prosthetic heart valve is implanted in an intended position and orientation. On the other hand, the term "outflow end," when used in connection with a prosthetic heart valve, refers to the end of the prosthetic heart valve through which blood exits when the prosthetic heart valve is implanted in an intended position and orientation. In the figures, like numbers refer to like or identical parts. As used herein, the terms "substantially," "generally," "approximately," and "about" are intended to mean that slight deviations from absolute are included within the scope of the term so modified. When ranges of values are described herein, those ranges are intended to include sub-ranges. For example, a recited range of 1 to 10 includes 2, 5, 7, and other single values, as well as all sub ranges within the range, such as 2 to 6, 3 to 9, 4 to 5, and others.

The present disclosure is generally directed to collapsible prosthetic mitral valves, and in particular various features thereof to provide controlled and predicable expression of the prosthetic mitral valve from a delivery device during deployment of the prosthetic valve into the native valve annulus. However, it should be understood that the features described herein may apply to other types of prosthetic heart valves, including prosthetic heart valves that are adapted for use in other heart valves, such as the tricuspid heart valve.

When a collapsible and expandable prosthetic heart valve is implanted into a patient, the prosthetic heart valve is typically first collapsed and stored within a sheath of a delivery device for transcatheter delivery, with the sheath holding the prosthetic heart valve in the collapsed condition during delivery. Once the delivery device is at or adjacent the native heart valve to be replaced, the prosthetic heart valve is ejected from the delivery device, for example by pushing the prosthetic heart valve distally out of the delivery device, or by withdrawing the sheath proximally relative to the prosthetic heart valve. As the overlying sheath begins to uncover the prosthetic heart valve, the prosthetic heart valve begins to transition to its shape-set condition (e.g. by self-expansion and balloon expansion). Preferably, as the prosthetic heart valve deploys from the delivery device, it deploys or expresses in a manner so that prosthetic valve leaflets coupled to the stent are not damaged by the stent deployment. Further, the prosthetic heart valve preferably deploys from the delivery device in a manner that does not damage the native anatomy. Finally, the prosthetic heart valve preferably can be deployed from the delivery device to the landing zone of the native heart valve in a repeatable fashion, so that the user can position the prosthetic heart valve in the desired anatomical position with minimal difficulty.

FIG. 1A illustrates an example of a collapsible and expandable prosthetic heart valve 100, according to the prior art, which may be particularly suited for replacement of a native mitral or tricuspid valve. It should be understood that the prosthetic heart valve 100 illustrated in FIG. 1A omits certain features that would typically be included, such as a valve assembly to assist in controlling blood flow through the prosthetic heart valve, and interior and/or exterior fabrics or tissue skirts to assist with providing a seal around in the prosthetic heart valve and/or with enhancing tissue ingrowth to fix the prosthetic heart valve within the native heart valve over time. However, for purposes of simplicity, the prosthetic leaflet(s) and skirt(s) are omitted from the drawings for clarity of illustration.

The prosthetic heart valve 100 is illustrated in FIG. 1A in an expanded configuration. The stent of the prosthetic heart valve 100 may include an outer stent or frame 101 and an inner stent or frame 105 positioned radially within the outer frame. The outer frame 101 may be primarily for anchoring the prosthetic heart valve 100 within the native heart valve annulus, while the inner frame 105 may be primarily for holding the prosthetic valve assembly in the desired position and orientation.

Figure 1B:
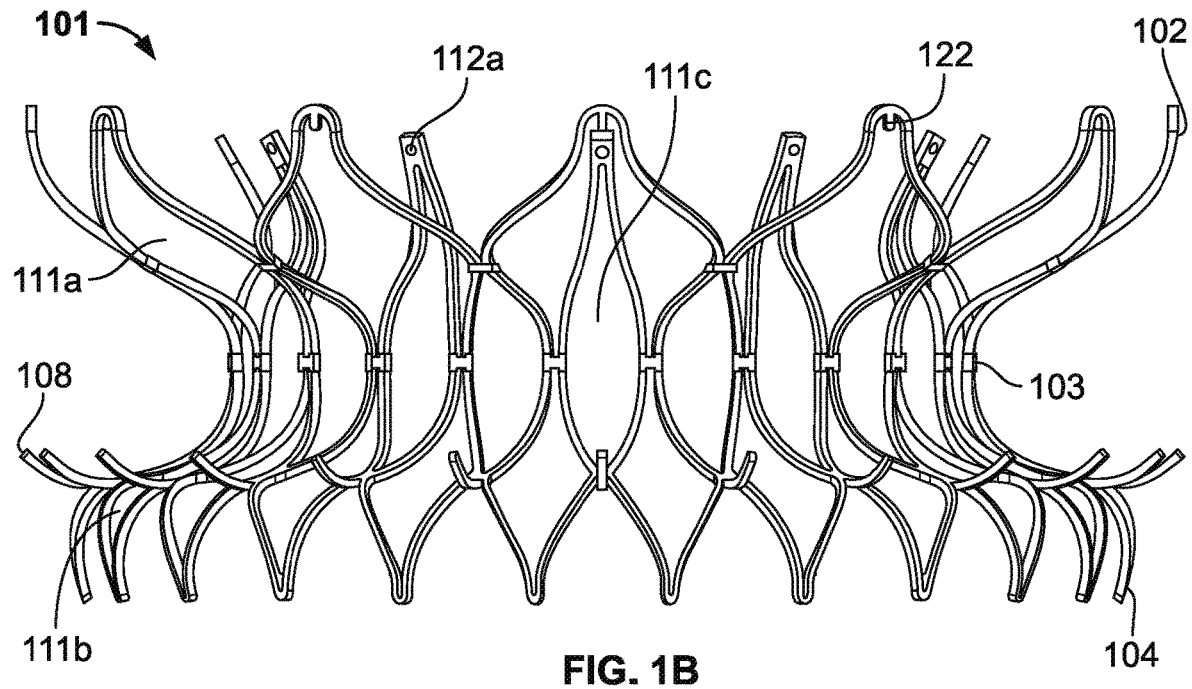
FIG. 1B is a perspective view of an outer frame of the stent frame of FIG. 1A.
Figure 1C:
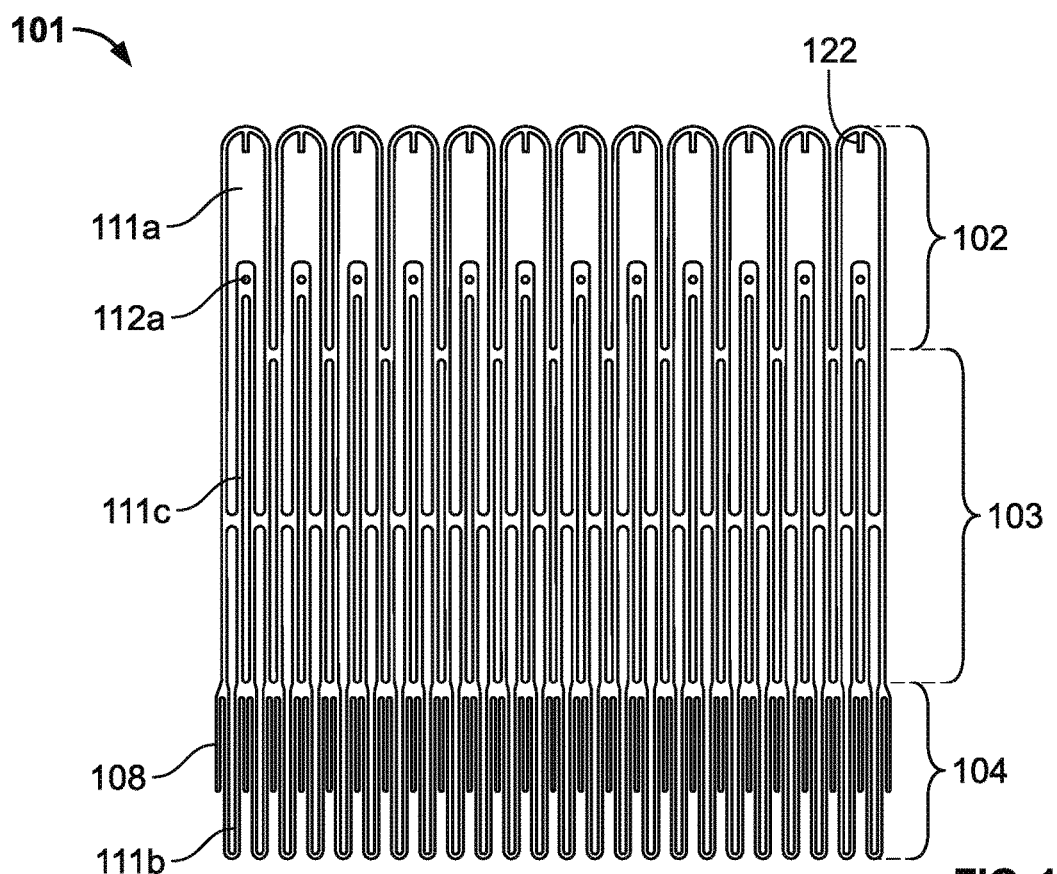
FIG. 1C is a flattened view of the outer stent of FIG. 1B, as if cut longitudinally and laid out flat on a table.

Outer frame 101 is illustrated in FIGS. 1B-C isolated from other components of the prosthetic heart valve 100. In FIG. 1B, the outer frame 101 is illustrated in an expanded condition. In FIG. 1C, the outer frame 101 is illustrated in a collapsed condition, as if cut longitudinally and laid flat on a table. As shown in FIGS. 1B-C, outer frame 101 may include an atrial portion or anchor 102, a ventricular portion or anchor 104, and a central portion 103 coupling the atrial portion to the ventricular portion. The central portion 103 may be between atrial portion 102 and ventricular portion 104. Atrial portion 102 may be configured and adapted to be disposed on an atrial side of a native valve annulus, and may flare radially outwardly from the central portion 103. Ventricular portion 104 may be configured and adapted to be disposed on a ventricle side of the native valve annulus, and may also flare radially outwardly from the central portion 103. The central portion 103 may be configured to be situated in the valve orifice, for example in contact with the native valve annulus. In use, the atrial portion 102 and ventricle portion 104 effectively clamp the native valve annulus on the atrial and ventricular sides thereof, respectively, holding the prosthetic heart valve 100 in place.

The atrial portion 102 may be formed as a portion of a stent or other support structure that includes or is formed by a plurality of generally diamond shaped cells, although other suitable cell shapes, such as triangular, quadrilateral, or polygonal may be appropriate. In some examples, the atrial portion 102 may be formed as a braided mesh, as a portion of a unitary stent, or a combination thereof. According to one example, the stent that includes the atrial portion 102 may be laser cut from a tube of nitinol and heat set to a desired shape so that the stent, including atrial portion 102, is collapsible for delivery, and re-expandable to the set-shape during deployment. The atrial portion 102 may be heat set into a suitable shape to conform to the native anatomy of the valve annulus to help provide a seal and/or anchoring between the atrial portion 102 and the native valve annulus. The heat-set atrial portion 102 may be partially or entirely covered by a cuff or skirt, on the luminal and/or abluminal surface of the atrial portion 102. The skirt may be formed of any suitable material, including biomaterials such as bovine pericardium, biocompatible polymers such as ultra-high molecular weight polyethylene, woven polyethylene terephthalate ("PET") or expanded polytetrafluoroethylene ("ePTFE"), or combinations thereof. The atrial portion 102 may include features for connecting the atrial portion to a delivery system. For example, the atrial portion 102 may include pins or tabs 122 around which sutures (or suture loops) of the delivery system may wrap, so that while the suture loops are wrapped around the pins or tabs 122, the outer frame 101 maintains a connection to the delivery device.

The ventricular portion 104 may also be formed as a portion the stent or other support structure that includes or is formed of a plurality of diamond shaped cells, although other suitable cell shapes, such as triangular, quadrilateral, or polygonal may be appropriate. In some examples, the ventricular portion 104 may be formed as a braided mesh, as a portion of a unitary stent, or a combination thereof. According to one example, the stent that includes the ventricular portion 104 may be laser cut from a tube of nitinol and heat set to a desired shape so that the ventricular portion 104 is collapsible for delivery, and re-expandable to the set-shape during deployment. The ventricular portion 104 may be partially or entirely covered by a cuff or skirt, on the luminal and/or abluminal surface of the ventricular portion 104. The skirt may be formed of any suitable material described above in connection with the skirt of atrial portion 102. It should be understood that the atrial portion 102 and ventricular portion 104 may be formed as portions of a single support structure, such as a single stent or braided mesh. However, in other embodiments, the atrial portion 102 and ventricular portion 104 may be formed separately and coupled to one another.

Figure 1D:
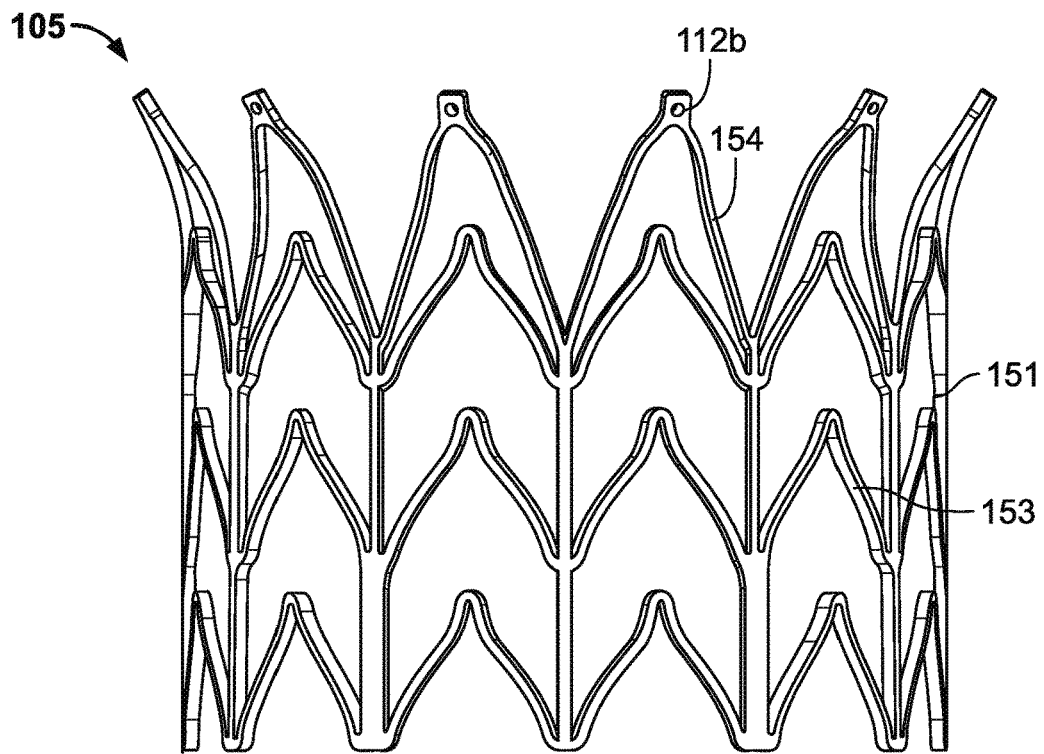
FIG. 1D is a perspective view of an inner frame of the stent frame of FIG. 1A.
Figure 1E:
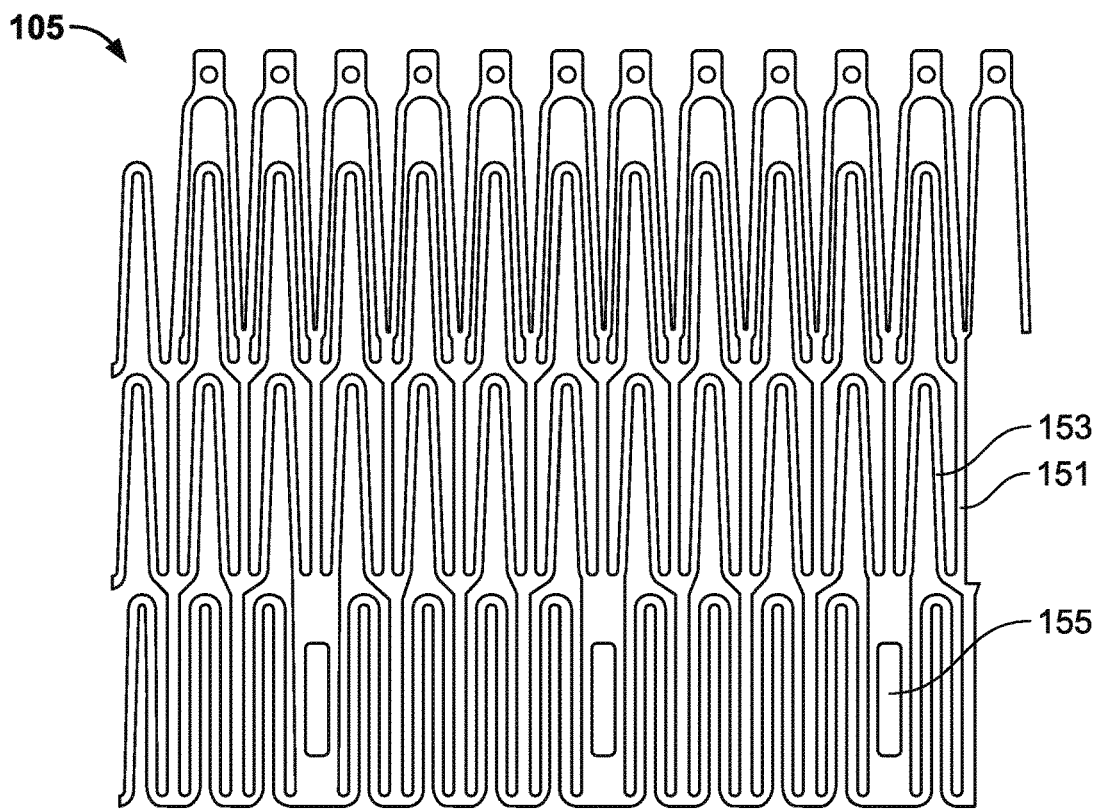
FIG. 1E is a flattened view of the inner stent of FIG. 1D, as if cut longitudinally and laid out flat on a table.

As illustrated in FIG. 1A, the inner frame 105 may be positioned radially within the outer frame 101 when the inner and outer frames are assembled together. Inner frame 105 is illustrated in FIGS. 1D-E isolated from other components of the prosthetic heart valve 100. In FIG. 1D, the inner frame 105 is illustrated in an expanded condition. In FIG. 1E, the inner frame 105 is illustrated in a collapsed condition, as if cut longitudinally and laid flat on a table. As shown in FIGS. 1D-E, the inner frame 105 may include a plurality of axially or longitudinally extending struts 151 and interconnecting v-shaped strut members 153. According to some embodiments, the inner frame 105 may have more or fewer v-shaped members 153 extending circumferentially around the diameter thereof than the number of cells in the atrial portion 102 and/or ventricular portion 104 of the outer frame 101, such as double or half the number. In some examples, the inner frame 105 may flare radially outwards at the atrial end, e.g., to conform to the flare of the atrial portion 102 of the outer frame 101. One or more prosthetic leaflets may be coupled to the inner frame 105 to form a prosthetic valve assembly, the prosthetic valve assembly configured to allow unidirectional flow of blood through the prosthetic valve assembly from the atrial end toward the ventricular end of the prosthetic heart valve 100. As best illustrated in FIG. 1E, the inner frame 105 may include a plurality of commissure windows 155 formed in axial struts 151. For example, inner frame 105 may include three generally rectangular shaped commissure windows 155 equidistantly spaced around the circumference of the inner frame, with each commissure window adapted to provide a location for coupling two adjacent prosthetic leaflets to the axial strut 151. However, more or fewer commissure windows 155 may be provided depending on how many prosthetic leaflets will be coupled to the inner frame 105.

The outer frame 101 and/or the inner frame 105 may formed of a superelastic and/or shape memory material such as nitinol. According to some examples, other biocompatible metals and metal alloys may be suitable. For example, superelastic and/or self-expanding metals other than nitinol may be suitable, while still other metals or metal alloys such as cobalt chromium or stainless steel may be suitable, particularly if the stent or support structure is intended to be balloon expandable. In some examples, the outer frame 101 and/or inner frame 105 may be laser cut from one or more tubes, such as a shape memory metal tube. The shape memory metal tube may be nitinol or any other bio-compatible metal tube. For example, the outer frame 101 may be laser cut from a first tube while the inner frame 105 may be laser cut from a second tube of smaller diameter.

The prosthetic heart valve 100 may be adapted to expand from a collapsed or constrained configuration to an expanded configuration. According to some examples, the prosthetic heart valve 100 may be adapted to self-expand, although the prosthetic heart valve could instead be partially or fully expandable by other mechanisms, such as by balloon expansion. The prosthetic heart valve 100 may be maintained in the collapsed configuration during delivery, for example via one or more overlying sheaths that restrict the valve from expanding. The prosthetic heart valve 100 may be expanded during deployment from the delivery device once the delivery device is positioned within or adjacent the native valve annulus. In the expanded configuration, the atrial portion 102 and ventricular portion 104 may extend radially outward from a central longitudinal axis of the prosthetic heart valve 100 and/or central portion 103, and may be considered to flare outward relative to the central longitudinal axis of the replacement valve and/or central portion 103. The atrial portion 102 and ventricular portion 104 may be considered flanged relative to central portion 103. The flared configuration of atrial and ventricular portions 102, 104 relative to central portion 103 is described in the context of a side view of the outer frame 101, as can be best seen in FIG. 1B. In some embodiments, the flared configuration of the atrial and ventricular portions 102, 104 and the central portion 103 may define a general hour-glass shape in a side view of the outer frame 101. That is, the atrial and ventricular portions 102, 104 may be flared outwards relative to the central portion 103 and then curved or bent to point at least partially back in the axial direction. It should be understood, however, that an hour-glass configuration is not limited to symmetrical configuration.

The outer frame 101 may be configured to expand circumferentially (and radially) and foreshorten axially as the prosthetic heart valve 100 expands from the collapsed delivery configuration to the expanded deployed configuration. As described herein, the outer frame 101 may define a plurality of atrial cells 111a in one circumferential row and a plurality of ventricular cells 111b in another circumferential row. Each of the plurality of cells 111a, 111b may be configured to expand circumferentially and foreshorten axially upon expansion of the outer frame 101. As shown, the cells 111a-b may each be diamond-shaped. In the illustrated embodiment, the outer frame 101 includes twelve atrial cells 111a, and twenty-four ventricular cells 111b. In addition, a third plurality of cells 111c in another circumferential row. Cells 111c may have a first end that is within a corresponding atrial cell 111a, at least when the frame is collapsed as shown in FIG. 1C. Cells 111c may have a second end that is positioned between pairs of adjacent ventricular cells 111b, at least when in the frame is collapsed as shown in FIG. 1C. In this particular example, the outer frame 101 includes twelve center cells 111c.

Still referring to FIGS. 1B-C, a pin or tab 122 may extend from an apex of each atrial cell 111a in a direction toward the outflow end of the outer frame 101. Although one pin or tab 122 is illustrated in each atrial cell 111a, in other embodiments fewer than all of the atrial cells may include a pin or tab. Each center cell 111c may include an aperture 112a or other coupling feature at a first apical end thereof for coupling to the inner frame 105, as is described in greater detail below. In the illustrated embodiment, the aperture 112a is positioned at the inflow apex of center cells 111c, and each center cell includes an aperture, although in other embodiments fewer than all of the cells may include such apertures. In the expanded condition of the outer frame 101, as shown in FIG. 1B, the apex of the center cells 111c that include the apertures 112a may be positioned radially inwardly of the apex of the atrial cells 111a near the inflow end of the outer frame. In addition, each center cell 111c may include a barb 108 extending from the opposite apex on the outflow send of the center cell, although fewer than all of the center cells may include such barbs. In the collapsed condition of the outer frame 101, as shown in FIG. 1C, each barb 108 extends toward the outflow end of the outer frame, each barb being positioned between two adjacent ventricular cells 111b. In the expanded condition of the outer frame 101, as shown in FIG. 1B, the barbs 108 may hook upwardly back toward the inflow end, the barbs being configured to pierce native tissue of the valve annulus, such as the native leaflets, to help keep the prosthetic heart valve from migrating under pressure during beating of the heart.

The inner frame 105 may be configured to expand circumferentially (and radially) while maintaining the same (or about the same) axial dimension (e.g., be non-foreshortening) as the prosthetic heart valve 100 expands from the collapsed delivery configuration to the expanded configuration. The axial struts 151 may contribute to this non-foreshortening functionality. By being non-foreshortening, the inner frame 105 may prevent (or reduce) strain from being placed on the prosthetic leaflets when the inner frame 105 transitions between the collapsed and expanded conditions. Thus, while the outer frame 101 may be designed to be foreshortening, the inner frame 105 may be designed so as to be substantially non-foreshortening.

Inner frame 105 may include twelve longitudinal struts 151, with three rows of twelve v-shaped members 153. However, in other embodiments, more or fewer longitudinal struts 151 may be included, and more or fewer rows of v-shaped members 153 may be included. In the illustrated embodiment, the number of longitudinal struts 151 is equal to the number of atrial cells 111a of the outer frame 101. In addition, v-shaped coupling members 154 may extend from each adjacent pair of longitudinal struts 151. These v-shaped coupling members 154 may have half-diamond shapes, with the apex of each half-diamond shape including an aperture 112b, the v-shaped coupling members generally flaring radially outwardly in the expanded condition of inner frame 105.

Referring back to FIG. 1A, in the expanded conditions of the outer frame 101 and the inner frame 105, the top portion of the center cells 111c may flare outwardly with a contour that substantially matches the outward flare of the v-shaped coupling members 154, so that apertures 112a and 112b align with each other. A coupling member, such as a rivet 112c, may pass through apertures 112a and 112b to couple the outer frame 101 to the inner frame 105.

Additional features and example replacement valves may be described in International patent application publication WO/2018/136959, filed Jan. 23, 2018, and titled "REPLACEMENT MITRAL VALVES," which is hereby incorporated by reference herein.

Figure 2A:
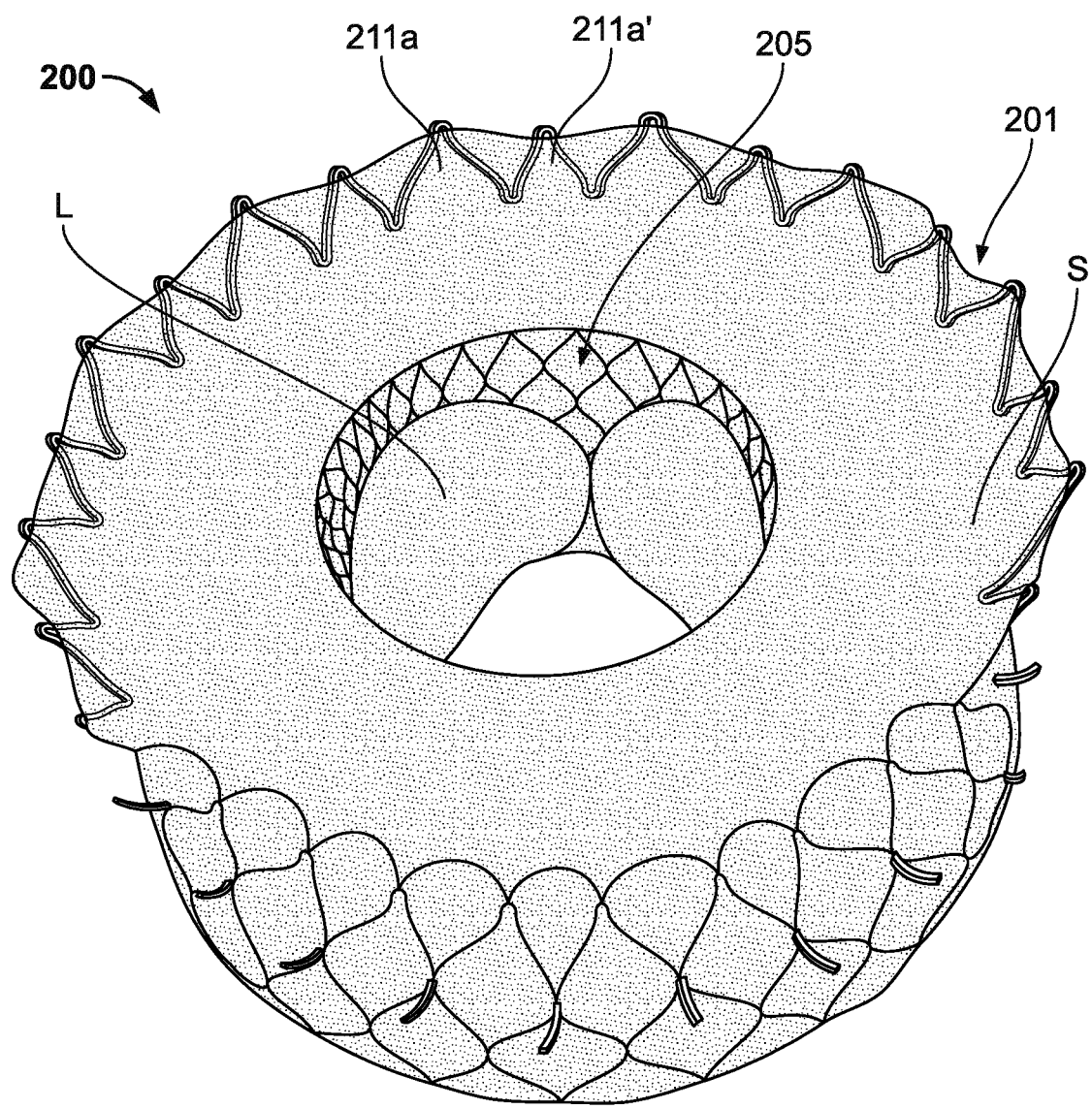
FIGS. 2A-B are perspective views from the atrial and ventricular sides, respectively, of a prosthetic heart valve according to another aspect of the disclosure.
Figure 2B:
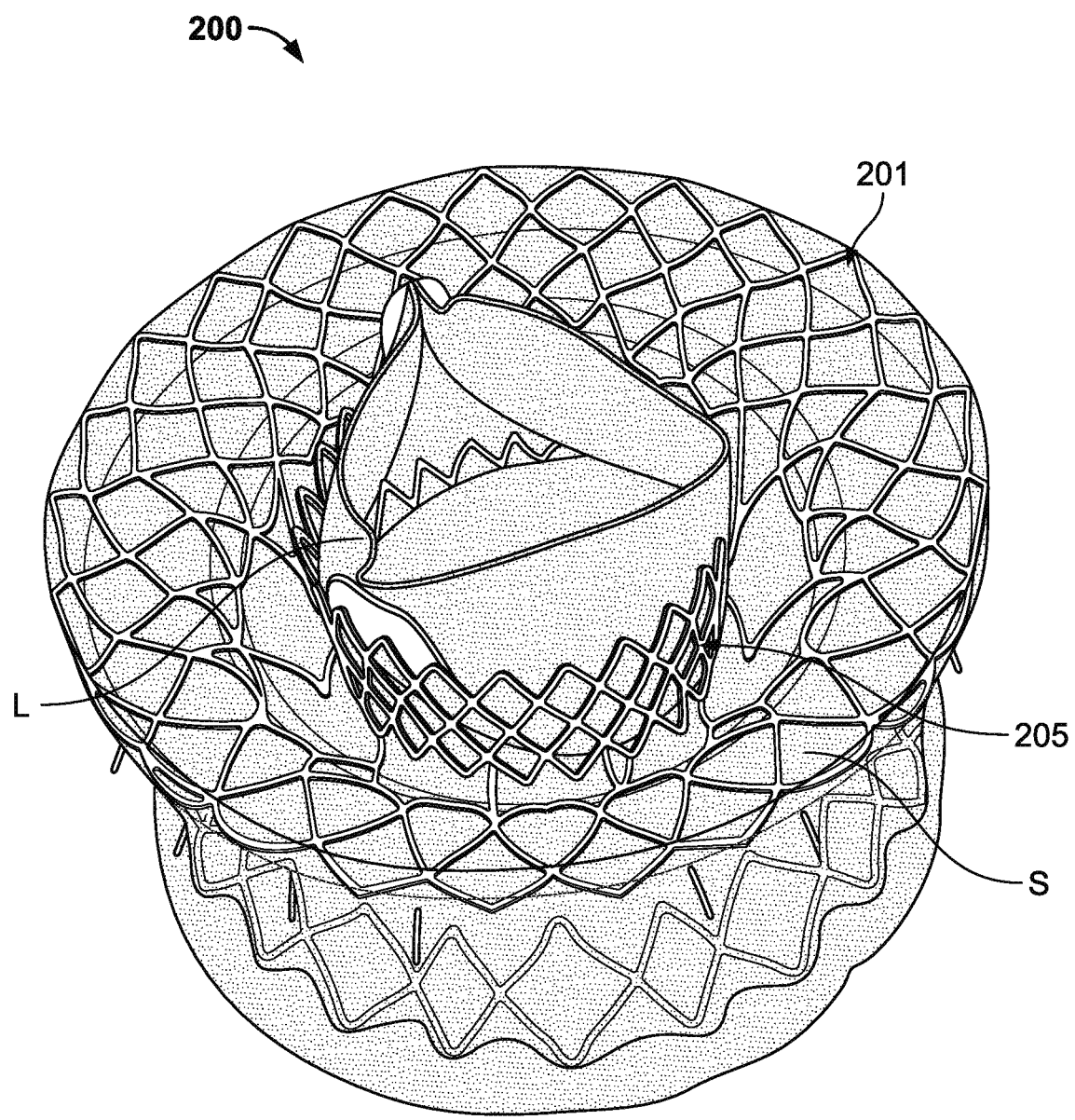

Another example of a prosthetic heart valve 200 is illustrated in an expanded condition in FIGS. 2A-B, with FIG. 2A illustrating the atrial side of the prosthetic heart valve and FIG. 2B illustrating the ventricular side of the prosthetic heart valve. Briefly, prosthetic heart valve 200 includes a plurality of prosthetic leaflets L coupled to the interior of an inner frame 205, with the prosthetic leaflets forming a valve assembly that is shown in FIGS. 2A-B in an open condition. Although three prosthetic leaflets L are shown, it should be understood that in other embodiments fewer or more than three prosthetic leaflets may be provided. The inner frame 205 may be positioned radially within, and coupled to, an outer frame 201. The outer frame 201 and inner frame 205 are described in greater detail below. Further, FIGS. 2A-B illustrate a skirt S, which may formed of fabric, tissue, or combinations thereof, on the inner frame 205 and/or outer frame 201. The skirt S may be formed of a single piece of material or multiple pieces of material, and may extend over any one or more of the luminal and abluminal surfaces of the inner frame 205 and the outer frame 201.

The overall general structure of prosthetic heart valve 200 may be substantially similar to that of prosthetic heart valve 100 in both structure and function, but prosthetic heart valve 200 may have various differences compared to prosthetic heart valve 100. For the purpose of brevity, the description below focuses on the differences between prosthetic heart valve 200 compared to prosthetic heart valve 100, with the remaining features of prosthetic heart valve 200 being similar or identical to the corresponding features of prosthetic heart valve 100.

Figure 2C:
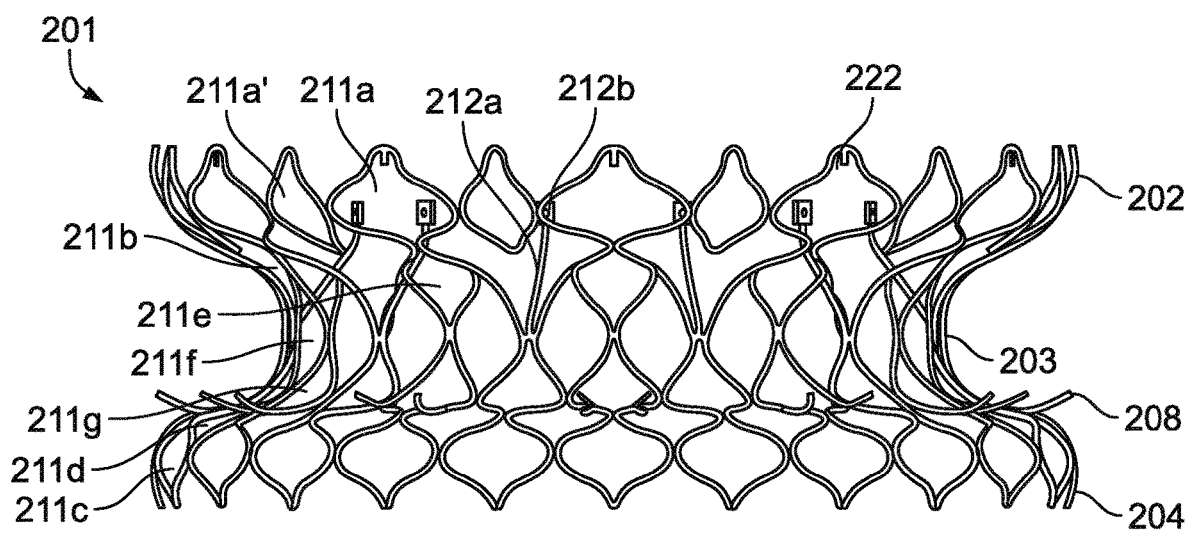
FIG. 2C is a perspective view of an outer frame of the prosthetic heart valve of FIGS. 2A-B.
Figure 2D:
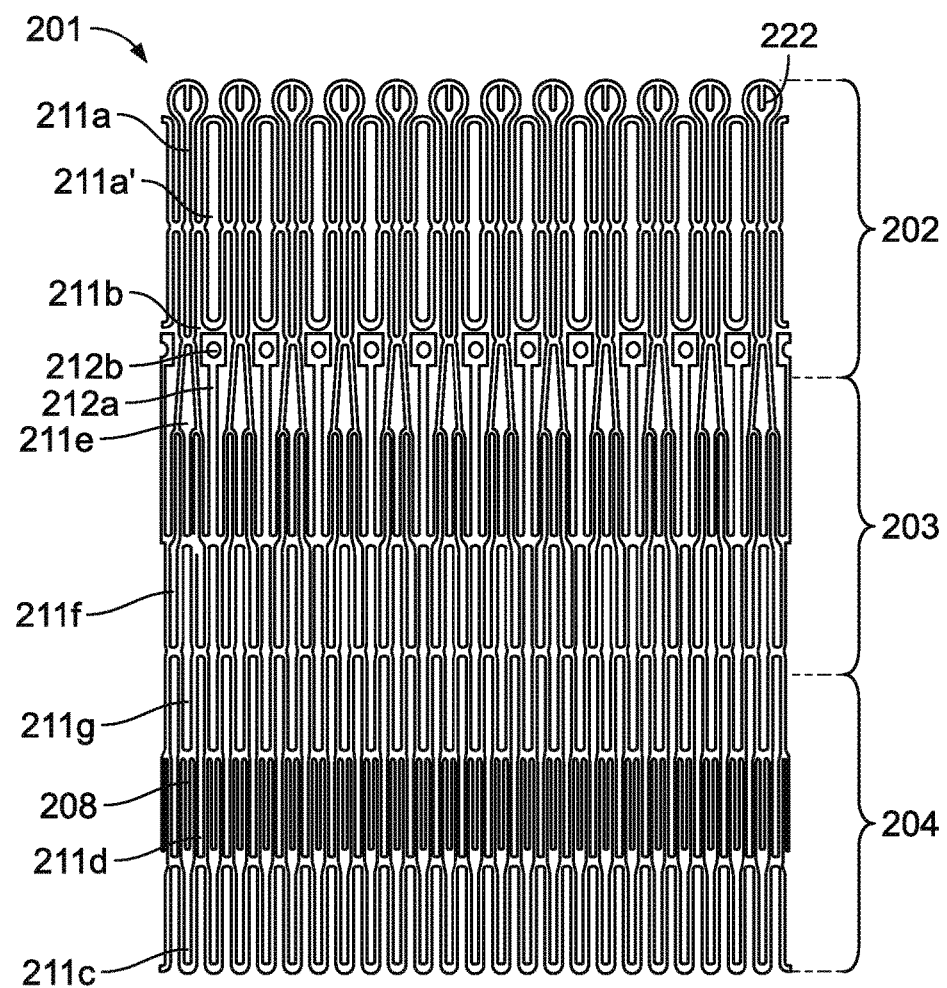
FIG. 2D is a flattened view of the outer frame of FIG. 2C, as if cut longitudinally and laid out flat on a table.

Outer frame 201 is illustrated in FIGS. 2C-D isolated from other components of the prosthetic heart valve 200. In FIG. 2C, the outer frame 201 is illustrated in an expanded condition. In FIG. 2D, the outer frame 201 is illustrated in a collapsed condition, as if cut longitudinally and laid flat on a table. Similar to outer frame 101, outer frame 201 may include an atrial portion or anchor 202, a ventricular portion or anchor 204, and a central portion 203 coupling the atrial portion to the ventricular portion.

The outer frame 201 may be configured to expand circumferentially (and radially) and foreshorten axially as the prosthetic heart valve 200 expands from the collapsed delivery configuration to the expanded deployed configuration. The inflow end of outer frame 201 may include a first row of atrial cells that include a first type of atrial cell 211a that alternates with a second type of atrial cell 211a'. The first type of atrial cells 211a and the second type of atrial cells 211a' may both be general diamond shaped, with the first type of atrial cells 211a being slightly wider than the second type of atrial cells 211a' in the circumferential direction. Outer frame 201 may include twelve of each type of atrial cell 211a, 211a' for a total of twenty four cells. Outer frame 201 may also include a second row of atrial cells 211b that are generally diamond-shaped, but for portions of the second type of atrial cell 211a' extending into the atrial cell 211b.

The outer frame 201 may include a plurality of ventricular cells 211c in a first row, and another plurality of ventricular cells 211d in a second row. The first row of ventricular cells 211c may be at the outflow end of the outer frame 201, and the second row of ventricular cells 211d may be positioned farther from the outflow end than, and adjacent to, the first row of ventricular cells 211c. In the illustrated embodiment the first and second rows of ventricular cells 211c, 211d are all generally diamond-shaped and have substantially the same, or an identical, size, with twenty-four cells in the first row of ventricular cells 211c and twenty-four cells in the second row of ventricular cells 211d.

Outer stent 201 is also illustrated as including three rows of center cells. A first row of center cells 211e is positioned adjacent the atrial end of the outer stent 201, each cell 211e being positioned between a pair of adjacent atrial cells 211b. Each center cell 211e may be substantially diamond-shaped, but it should be understood that adjacent center cells 211e do not directly touch one another. The first row of center cells 211e may include twelve center cells 211e. A second row of center cells 211f may be positioned at a longitudinal center of the outer frame 201, each center cell 211f being positioned between an atrial cell 211b and center cell 211e. In the illustrated embodiment, center cells 211f in the second row may be diamond-shaped, with the second row including twenty-four center cells 211f. Finally, a third row of center cells 211g may be positioned between the second row of center cells 211f and the second row of ventricular cells 211d. The third row of center cells 211g may include twenty-four cells and they may each be substantially diamond-shaped.

Figure 2E:
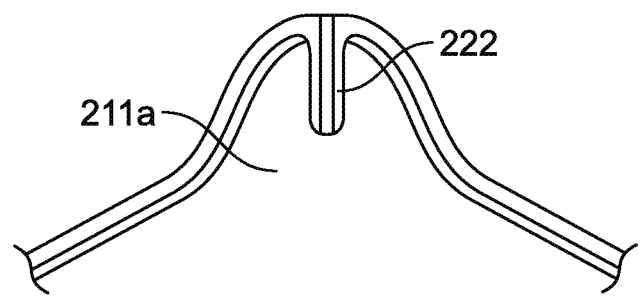
FIG. 2E is an enlarged view of an atrial tip portion of the outer frame of FIG. 2C in the expanded condition.
Figure 2F:
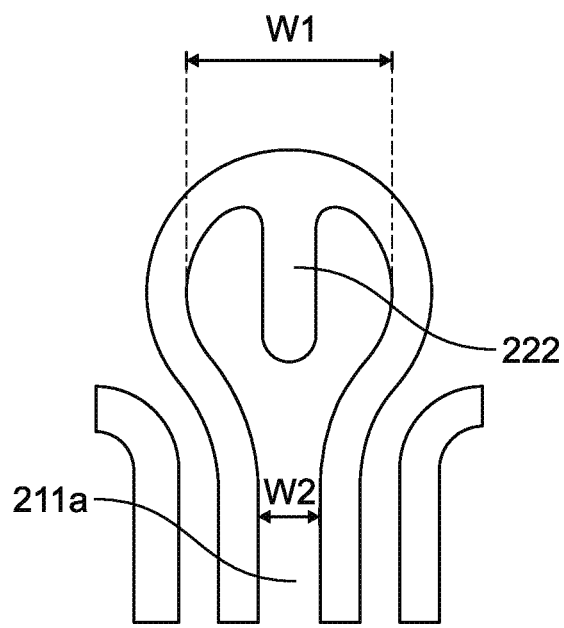
FIG. 2F is an enlarged view of the atrial tip portion of the outer frame of FIG. 2C in the collapsed condition.

All of the cells 211a-g may be configured to expand circumferentially and foreshorten axially upon expansion of the outer frame 201. Similar to outer frame 101, outer frame 201 may include pins or tabs 222 extending from an outflow apex of each atrial cell 211a in the first row in a direction toward the outflow end of the outer frame 201. However, if twelve pins or tabs 222 are provided, they may be provided in the wider first type of atrial cell 211a, and omitted from the narrower second type of atrial cell 211a'. FIG. 2E is an enlarged view of a portion of one of the atrial cells 211a of the first type in an expanded condition, with pin or tab 222 shown. As can be seen in FIG. 2E, when the outer frame 201 is expanded, there is a relatively large amount of clearance around the pin or tab 222. With this configuration, after the outer frame 201 is fully expanded, it may be relatively easy to withdraw any suture loops that are positioned around the pin or tab 222, for example by advancing the suture loops forward toward and then beyond the free end of the pin or tab. When the outer frame 201 is in the collapsed condition, however, the clearance around the pin or tab 222 may significantly reduce, as shown in FIG. 2F. For example, the open space within atrial cell 211a adjacent the pin or tab 222 may be a first relatively large width W1 when the outer frame 201 is collapsed, but the remainder of the atrial cell may have an open space that is a relatively small width W2. By narrowing the open space W2 compared to open space W1, while the outer frame 201 is collapsed, any suture or suture loops surrounding the pin or tab 222 will be less likely to unintentionally detach, since the available space for the suture loops to move is reduced. However, once the outer frame 201 is expanded, as shown in FIG. 2E, there is a large amount of open space adjacent the pin or tab 222 to allow the suture loop to be disconnected to disconnect the outer frame 201 from the delivery device.

Whereas outer frame 101 included apertures 112a at an apex of a center cell 111c, outer frame 201 may instead include coupling arms 212a. Each coupling arm 212a may be a strut that is coupled to a bottom or outflow apex of each atrial cell 211b in the second row, with each strut extending toward the inflow end of the outer frame 201 to a free end of the coupling arm 212a. The free end of each coupling arm 212a may include an aperture 212b for coupling to the inner frame 205, as described in greater detail below. In the collapsed condition, as best shown in FIG. 2D, each coupling arm 212a is substantially surrounded by an atrial cell 211b in the second row. In the expanded condition, best shown in FIG. 2C, the coupling arms 212a may extend radially inwardly and have a contour so that the free end extends substantially parallel to the center longitudinal axis of the outer frame 201. In addition, outer frame 201 may include a plurality of barbs 208 extending from a center portion or ventricular portion of the outer frame for piercing native tissue in the native annulus or in the native leaflets. In the illustrated embodiment, each barb 208 is connected to a ventricular cell 211d in the second row. In some embodiments, the barb 208 may be coupled to an inflow or outflow apex of each cell. In the particular illustrated embodiment, the barbs 208 are couple to ventricular cells 211d on an inflow half of the cell, on either side of the inflow apex. For example, the barb 208 in one ventricular cell 211d may be coupled to the inflow half of that cell on a right side of the apex, with the adjacent ventricular cell 211d having a barb coupled to the inflow half of that cell on a left side of the apex. With this configuration, the barbs 208 are provided in pairs with relatively little space between the barbs of a pair, but a relatively large space between adjacent pairs. In the collapsed condition of the outer frame 201, as shown in FIG. 2D, each barb 208 extends toward the outflow end of the outer frame, each barb being positioned within a ventricular cell 211d in the second row. In the expanded condition of the outer frame 201, as shown in FIG. 2C, the barbs 208 may hook upwardly back toward the inflow end, the barbs being configured to pierce native tissue of the valve annulus, such as the native leaflets, to help keep the prosthetic heart valve from migrating under pressure during beating of the heart.

Figure 2G:
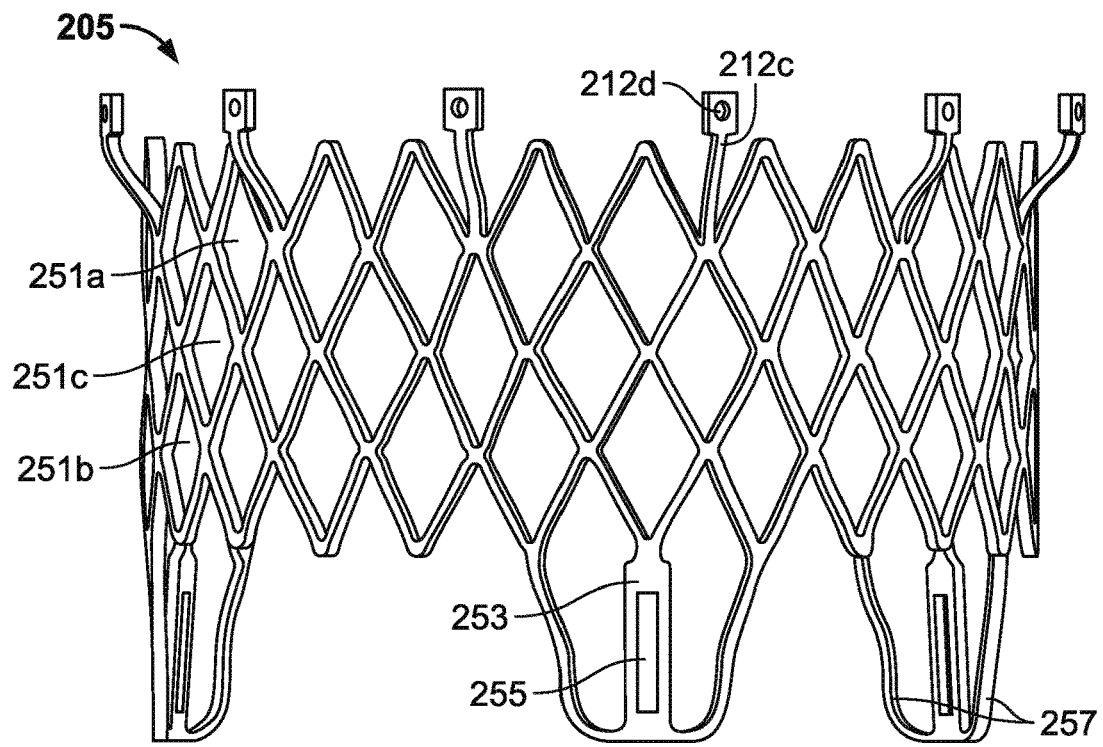
FIG. 2G is a perspective view of an inner frame of the prosthetic heart valve of FIGS. 2A-B.
Figure 2H:
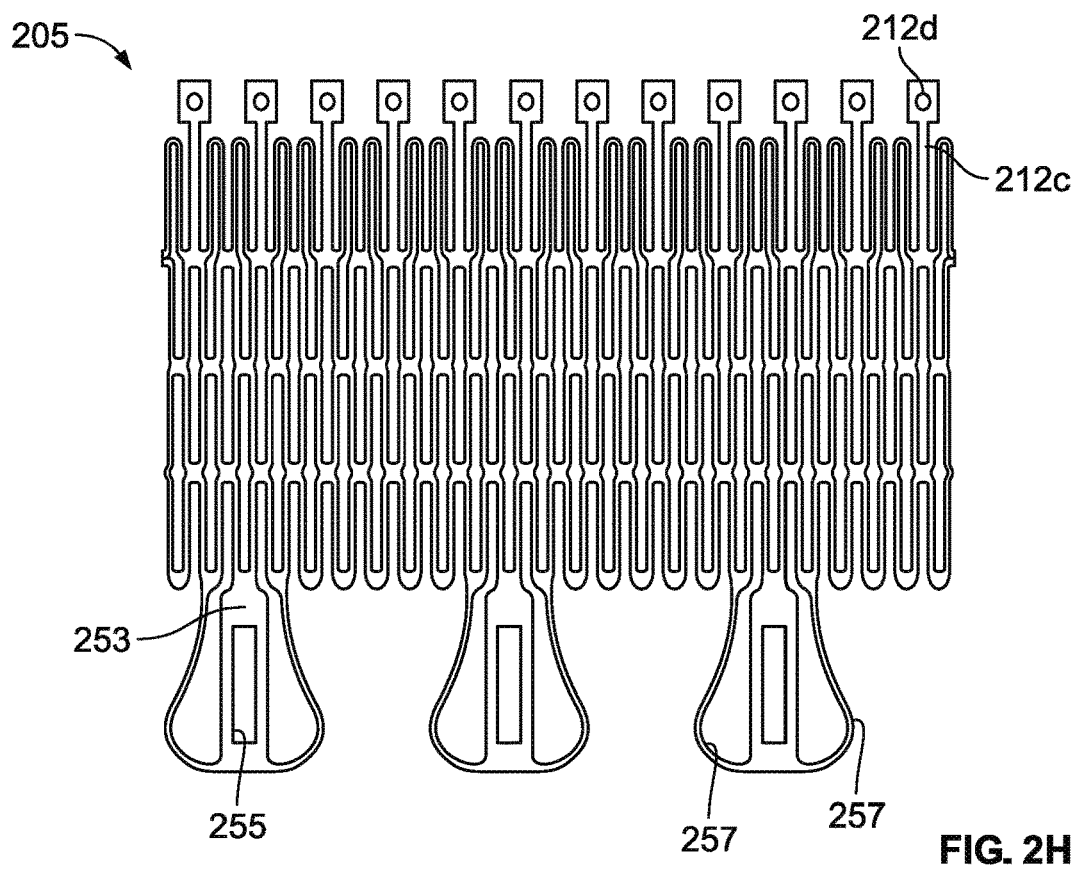
FIG. 2H is a flattened view of the inner frame of FIG. 2G, as if cut longitudinally and laid out flat on a table.

As illustrated in FIGS. 2A-B, the inner frame 205 may be positioned radially within the outer frame 201 when the inner and outer frames are assembled together. Inner frame 205 is illustrated in FIGS. 2G-H isolated from other components of the prosthetic heart valve 200. In FIG. 2G, the inner frame 205 is illustrated in an expanded condition. In FIG. 2H, the inner frame 205 is illustrated in a collapsed condition, as if cut longitudinally and laid flat on a table. Whereas inner frame 105 includes longitudinal struts 151 and is non-foreshortening, inner frame 205 instead includes a plurality of rows of diamond-shaped cells so that the inner frame 205 foreshortens upon expansion. In the illustrated example, inner frame 205 includes three rows of diamond-shaped cells, including a first row of cells 251a at the inflow end of the inner frame, a second row of cells 251b at the outflow end of the inner frame, and a third row of cells 251c positioned between the first and second rows. In some embodiments, the inner frame 205 may include more or fewer rows of cells. In the expanded condition shown in FIG. 2G, the three rows of cells 251a-c may be substantially cylindrical.

As shown in FIGS. 2A-B, one or more prosthetic leaflets L may be coupled to the inner frame 205 to form a prosthetic valve assembly, the prosthetic valve assembly configured to allow unidirectional flow of blood through the prosthetic valve assembly from the atrial end toward the ventricular end of the prosthetic heart valve 200. As illustrated in FIGS. 2G-H, the inner frame 205 may include a plurality of commissure windows 255 formed in axial struts 253 extending from selected cells 251b at the outflow end of the inner frame 205. For example, inner frame 205 may include three generally rectangular shaped commissure windows 255 equidistantly spaced around the circumference of the inner frame, with each commissure window adapted to provide a location for coupling two adjacent prosthetic leaflets to the axial strut 253. However, more or fewer commissure windows 255 may be provided depending on how many prosthetic leaflets will be coupled to the inner frame 205. Additional support struts 257 may connect the axial struts 253 to the cells 251b. In particular, a first support strut 257 may couple the outflow end of each axial strut 253 to the outflow apex of a first cell 251b on a first side of the axial strut, and a second support strut 257 may couple the outflow end of each axial strut 253 to the outflow apex of a second cell 251b on a second opposite side of the axial strut, with the axial strut coupled to a third cell 251b between the first and second cells. As shown in FIGS. 2G-H, the support struts 257 may be contoured so as to avoid presenting any sharp tips, which may help avoid damaging the anatomy.

The inner frame 205 may also include a plurality of coupling arms 212c. Each coupling arm 212c may have a first end coupled to the inner frame 205 at an inflow end of the inner frame. In particular, the first end of each coupling arm 212c may be attached to a junction between two adjacent cells 251a in the first row at the inflow end. The coupling arms 212c may extend in a direction away from the outflow end of the inner frame 205 to a free end, with the free end including an aperture 212d therein. In the expanded condition, as shown in FIG. 2G, the coupling arms 212c may initially extend radially outwardly from the inner frame 205, with the free end being contoured so that the free end extends substantially parallel to the longitudinal axis of the inner frame 205. In the illustrated embodiment, inner frame 205 may include a total of twelve coupling arms 212c spaced equidistantly around the circumference of the inner frame. Preferably, the number of coupling arms 212c corresponds to the number of coupling arms 212a. Coupling members, such as a rivets, may pass through apertures 212b and 212d to couple the outer frame 201 to the inner frame 205.

Figure 3:
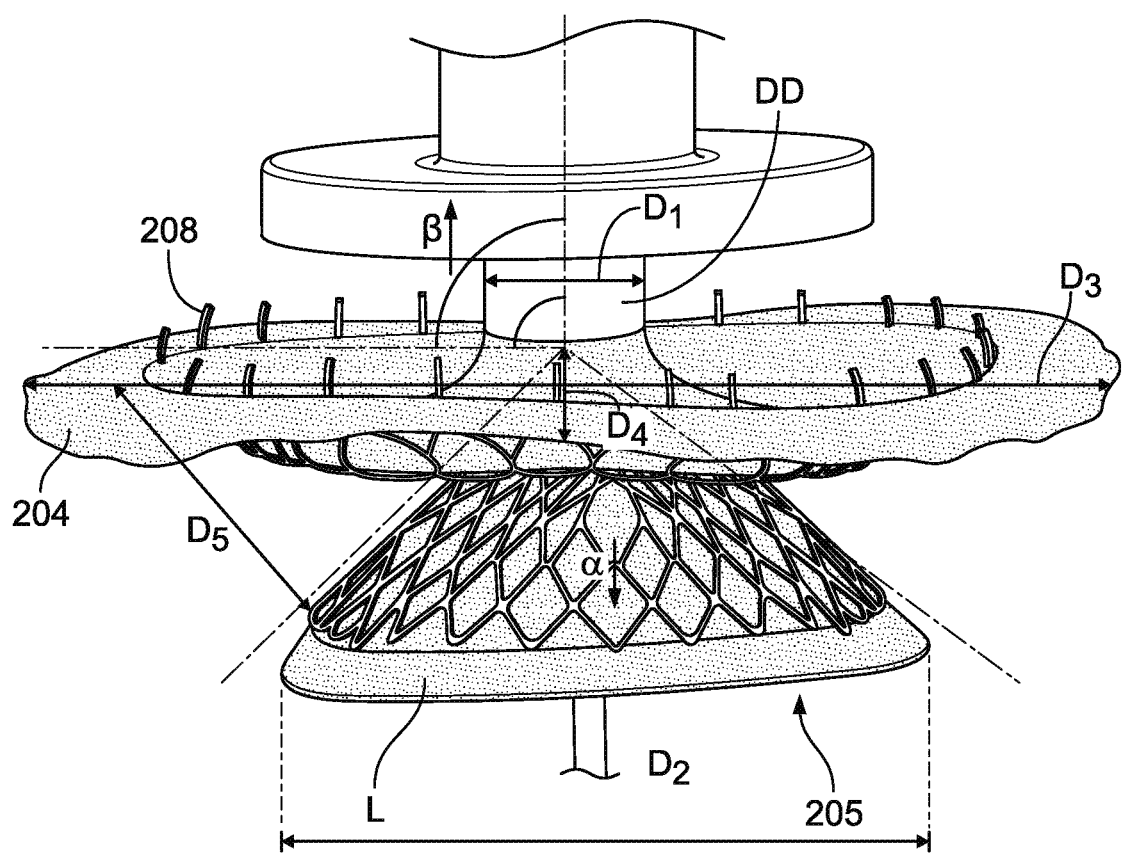
FIG. 3 is a side view of the prosthetic heart valve of FIGS. 2A-B being deployed from an overlying sheath of a delivery device.

As noted above, it is generally preferable that as prosthetic heart valve 100 or 200 deploys from a delivery device, it deploys or expresses in a manner so that prosthetic valve leaflets coupled to the stent are not damaged by the stent deployment. This preference not only applies to prosthetic heart valve 100 and 200, but other prosthetic heart valves having generally similar configurations. One potential way in which the prosthetic valve leaflets of prosthetic heart valves 100, 200 may be damaged during valve expression is illustrated in FIG. 3. FIG. 3 illustrates prosthetic heart valve 200 mid-deployment from an overlying sheath of a delivery device DD. In particular, FIG. 3 illustrates the ventricular or outflow end of inner frame 205 in the process of self-expanding while the atrial or inflow end of the inner frame 205 remains collapsed within the distal end of the overlying sheath of the delivery device DD. Further, the ventricular anchors 204, including barbs 208, have been deployed from the delivery device DD in FIG. 3, while the atrial portion 202 and part of the central portion 203 of the outer frame 201 remains collapsed within the distal end of the overlying sheath of the delivery device DD. During the stage of deployment or expression illustrated in FIG. 3, the atrial end or inflow end of the prosthetic heart valve 200 remains constrained to the size of the inner diameter D1 of the distal end of the overlying sheath of the delivery device DD, while the ventricular end or outflow end attempts to expand to its unbiased or set-shape. However, due to the atrial or inflow end of the prosthetic heart valve 200 still being constrained by the inner diameter D1 of the delivery device DD, the outflow end of the inner frame 205 may tend to over-expand prior to full release of the prosthetic heart valve 200 from the delivery device DD. In other words, referring to FIG. 3, the outflow end of the inner frame 205 may self-expand to a diameter D2 during expression of the prosthetic heart valve 200 from the delivery device DD when the inflow end of the prosthetic heart valve 200 (including the inflow end of the inner frame 205) remains constrained by the delivery device. The illustrated diameter D2 is larger than the shape-set diameter of the outflow end of the inner frame 205. In other words, during expression of the prosthetic heart valve 200, the outflow end of the inner frame 205 may temporarily expand to a size larger than the size the inner frame 205 is intended to have when in the unbiased and/or implanted condition. One result of this tendency is that the prosthetic leaflets L, which may be coupled to the inner frame 205 at commissure windows 255, may temporarily stretch beyond the intended amount, and such over-stretching could damage the prosthetic leaflets L, which may result in decreased durability of the prosthetic heart valve 200. It should be understood that although prosthetic heart valve 200 is illustrated in FIG. 3, the concept applies with similar or equal force to prosthetic heart valve 100, as well as other prosthetic heart valves that include similar configurations, whether the frame to which the prosthetic leaflets are attached is foreshortening or non-foreshortening.

Figure 4A:
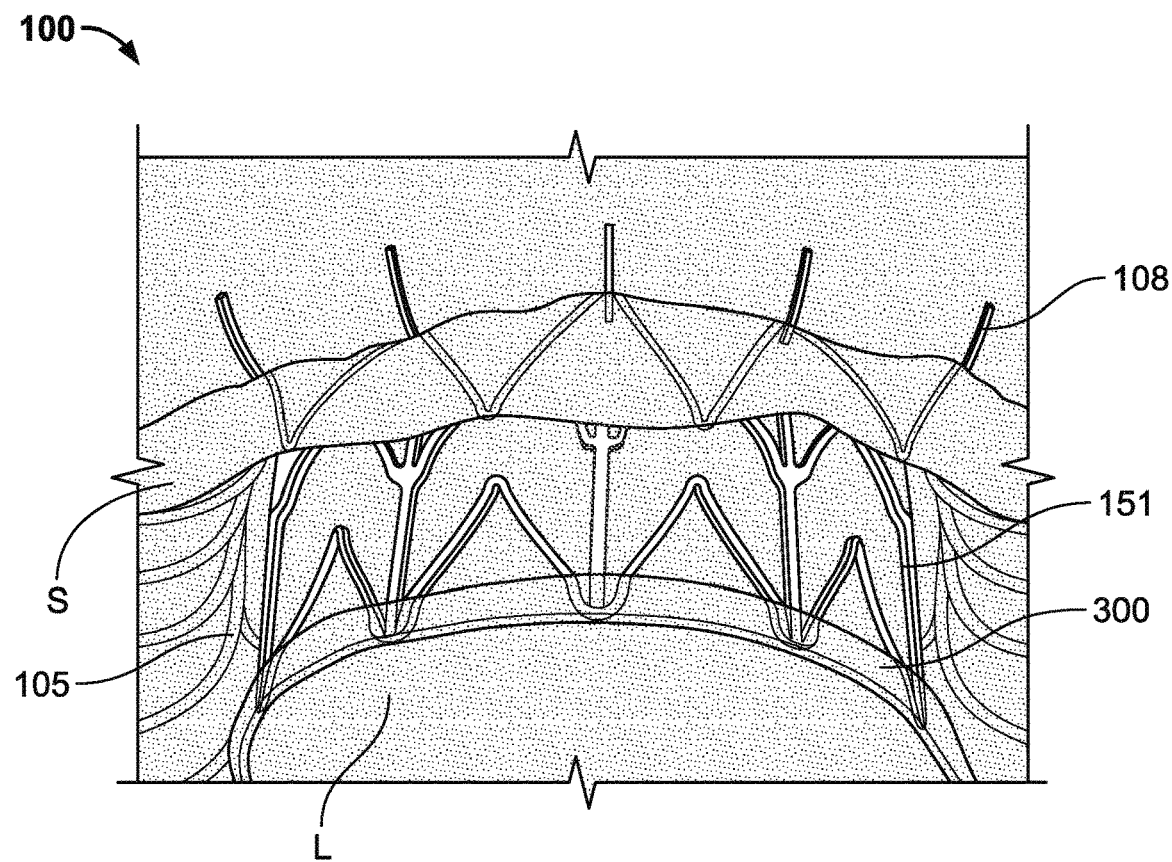
FIG. 4A is a perspective view of the prosthetic heart valve of FIG. 1A including a constraining member according to one aspect of the disclosure.

One option to limit the potential over-stretching of the prosthetic leaflets described above is to provide a physical constraint on the expansion of portions of the prosthetic heart valve. For example, FIG. 4A is a perspective view of prosthetic heart valve 100 with a constraining feature. In particular, prosthetic heart valve 100 in FIG. 4A includes a constraining member 300 to limit the expansion of the inner frame 105. In the particular illustrated example, constraining member 300 is a woven PET band that is coupled to the outflow or ventricular end of the inner frame 105. In this example, the constraining member 300 is in the form of a generally tube or ring shaped member that extends circumferentially around the inner perimeter and/or outer perimeter of the ventricular end of the inner frame 105. The constraining member 300 is illustrated as having a minimal height in the axial direction, extending only over the tips of the axial struts 151. However, in other embodiments the constraining member 300 may have a greater height than illustrated. The constraining member 300 may be coupled to the inner frame 300-105 via any suitable mechanism, for example by sutures, adhesives, or any other suitable mechanism. The constraining member 300 illustrated in FIG. 4A is a woven PET band, but it should be understood that other materials may be suitable, including suture rings, weaves, and/or tubes of other woven or non-woven synthetic fabrics or even tissue materials. However, it is preferable that the constraining member 300 be inelastic (e.g. an inelastic band) or otherwise have relatively low elasticity. In other words, one purpose of the constraining member 300 is to limit expansion of the inner frame 105, so it is desirable that the constraining member 300 does not easily stretch. It should be understood that the term inelastic, as used herein, is not limited to the mathematical definition of inelastic. Rather, the term inelastic, as used herein, refers to materials that are generally resistant to stretching upon application of typical forces on a prosthetic heart valve during the deployment and operation of the prosthetic heart valve. The exact position of the constraining member 300 in the axial direction of the inner frame 105 may also be other than that shown. For example, while constraining member 300 is illustrated positioned at the terminal outflow end of the inner frame 105, in other embodiments the constraining member 300 may be positioned a spaced axial distance from the terminal outflow end of the inner frame 105. However, the closer the constraining member 300 is positioned to the terminal outflow end of the inner frame 105, the greater the constraint will be on the expansion of the inner frame 105, all else being equal. Thus, it may be preferable to position the constraining member 300 to at least cover the terminal outflow end of the inner frame 105.

Figure 4B:
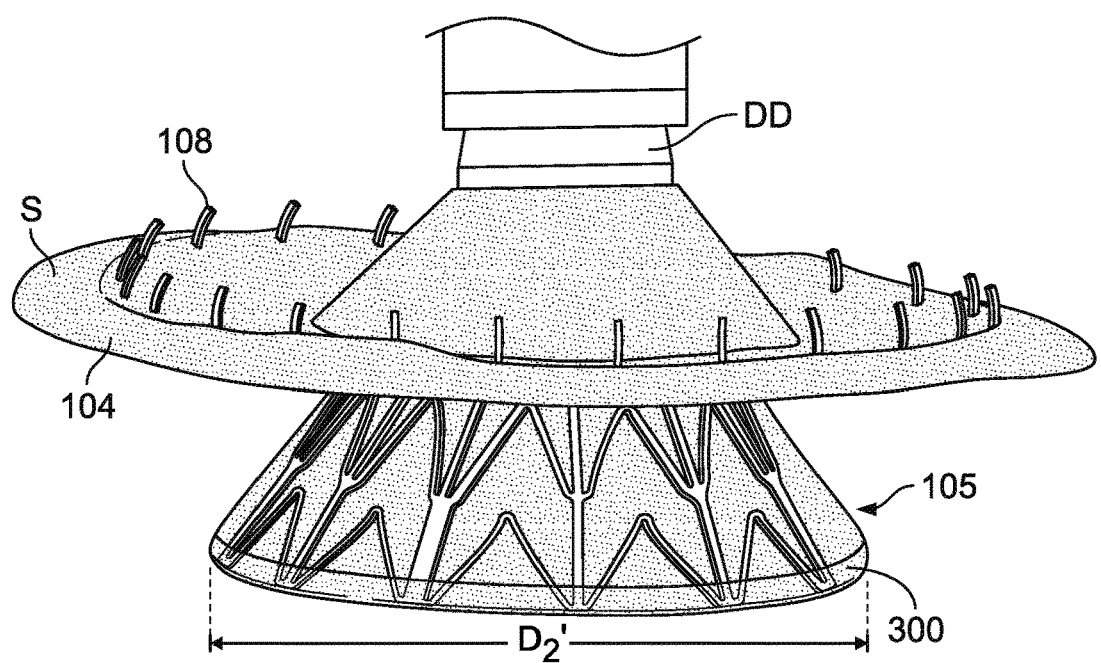
FIG. 4B is a side view of the prosthetic heart valve of FIG. 4A being deployed from an overlying sheath of a delivery device.

As illustrated in FIG. 4B, as the prosthetic heart valve 100 is deployed or expressed from the overlying sheath of the delivery device DD, the constraining member 300 limits the expansion of the outflow end of the inner frame 105 to a diameter of D2', which is significantly smaller than the diameter D2 shown in FIG. 3. Thus, the prosthetic leaflets L, and particular the free edges of the prosthetic leaflets, will stretch less (or avoid stretching) than they would in the absence of constraining member 300. The prosthetic leaflets L may include attached ends and free ends, the free ends adapted to coapt with one another to allow unidirectional flow of blood through the prosthetic heart valve 100. The free edges of the prosthetic leaflets may be generally aligned axially with the constraining member 300. It should be understood that, although FIG. 3 illustrates inner frame 205 and FIG. 4B illustrates inner frame 105, the effect of the constraining member 300 on limiting the expansion of the inner frame (compare diameter D2' to diameter D2) applies equally to both types of inner frames. Thus, it should be understood that constraining member 300 may be applied in substantially the same manner to inner frame 205 with substantially similar or identical results.

Figure 5A:
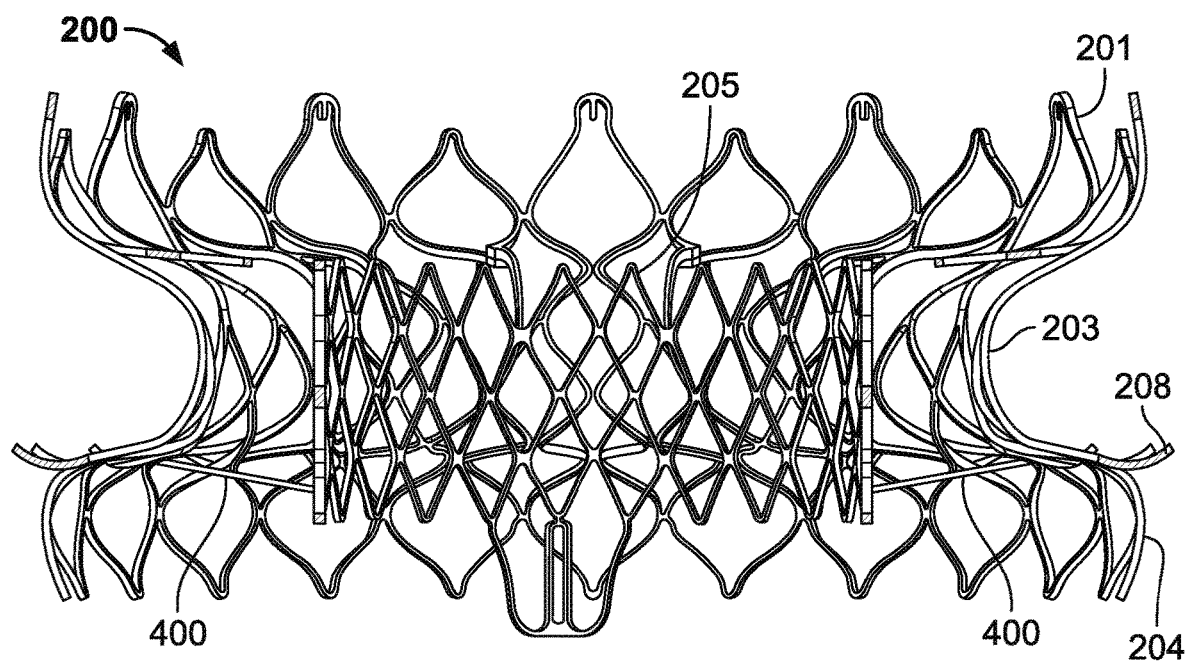
FIGS. 5A-B are side and bottom views, respectively, of the prosthetic heart valve of FIGS. 2A-B including a constraining member according to another aspect of the disclosure.

As noted above, it is generally preferable that as prosthetic heart valve 100 or 200 deploys from a delivery device, the valve expression is sequenced to avoid damage to the native tissue and so that accurate deployment is repeatable. FIG. 5A illustrates prosthetic heart valve 200 with one or more constraining members 400 that may help achieve one or more of these goals. It should be understood that the prosthetic heart valve 200 in FIG. 5A omits the prosthetic leaflets L and skirt S for clarity of illustration. In addition, the disclosure regarding constraining members 400 may apply with equal force to prosthetic heart valve 100, and other prosthetic hearts valves having a generally similar configuration. Constraining members 400 may be a plurality of individual constraining members, or a single constraining member. For example, as illustrated in FIG. 5A, a plurality of individual constraining members 400 each extend from a ventricular or outflow end of the inner frame 205 (or a position adjacent to the outflow end) to the ventricular anchor 204 of outer frame 201. While the exact point of connection between the constraining members 400 and the outer frame 201 may vary, in the illustrated embodiment, the point of connection may be at or near where the central waist portion 203 of the outer frame 201 transitions to the ventricular anchors 204, including adjacent to the point where barbs 208 are coupled to the outer frame 201. However, the constraining members 400 may couple to the frame at any location from the central waist portion 203 to the tips of the ventricular anchors 204. The constraining members 400 may take various different suitable forms. For example, constraining members 400 may be individual strips of material, which may be generally similar to constraining member 300 (e.g. a woven fabric such as PET, or other generally inelastic strip of synthetic fabric or tissue material). In other embodiments the constraining members may take the form of suture connections, or other materials such as metal or metal alloy wires, such as nitinol wires. In some embodiments, the constraining members 400 may be used in conjunction with constraining member 300. For example, constraining members 400 may be separate from, but connected to, constraining member 300. Or, in other embodiments, the constraining members 400 may be integral with the constraining member 300, for example forming individual extensions from the constraining member 300. In other embodiments, the constraining members 400 may be formed as a single constraining member 400, for example an annular or doughnut shaped member, that surrounds the inner frame 205 and coupled at locations around its outer circumference to the outer frame 201. And although the constraining members 400 are illustrated as connecting to the outer frame 201 at or near the transition between the central waist portion 203 and the ventricular anchors 204, the connection point may be instead located closer to the outflow end of the outer frame 201 or closer to the inflow end of the outer frame 201. By being inelastic, substantially inelastic, or otherwise resistant to stretching when subjected to forces typically experienced during use as part of a prosthetic heart valve, the length of the constraining members 400 between the inner frame 205 and outer frame 201 remains substantially unchanged. Referring to FIG. 3, this length is represented by length D5. Thus, constraining members 400 may serve to limit length D5 to a maximum value that is substantially equal to the length of the constraining members 400. Certain benefits of limiting length D5 are described in greater detail below.

Still referring to FIG. 3, one result of constraining members 400 limiting length D5 is that length D3 may also be limited. Generally, length D3 refers to the diameter of the ventricular anchor 204 when expanded. By limiting length D3, as the prosthetic heart valve 200 (or 100) is deployed from an overlying sheath of the delivery device DD, the ventricular anchor 204, and particularly the barbs 208, will help prevent premature engagement of the outer frame 201 with the native valve annulus and adjacent anatomy. In other words, as the prosthetic heart valve 200 is released from the delivery device, the ventricular or outflow ends of the inner frame 205 and outer frame 201 begin to expand first on the ventricular side of the native valve annulus. As the ventricular anchor 204 transitions from the collapsed condition to the expanded condition, the constraining members 400 limit length D5 which in turns limits the rate at which the ventricular anchor 204 reaches its fully expanded condition, as well as limiting the overall length D3 in general, helping to insure that the length D3 does not exceed (even temporarily during deployment) the length D3 is intended to have in a fully deployed configuration. By limiting this rate, as well as generally constraining the length D3, the constraining members 400 delay the rapidity with which the barbs 208 of the ventricular anchor 204 engage anatomical tissue, including the native valve leaflets, the sub-valvular apparatus, and/or myocardium. This delay may help ensure that the remainder of the prosthetic heart valve 200 is in the desired position and orientation with respect to the native valve annulus prior to the barbs 208 engaging the native tissue. Once the barbs 208 engage the native tissue, the ability to reposition or reorient the prosthetic heart valve 200 may be limited. Thus, by delaying engagement of the ventricular anchor 204 with the native valve annulus, it may be easier to properly position and orient the prosthetic heart valve 200 within the native valve annulus. Further, if during deployment, the length D3 increased above the intended length D3 when fully deployed, negative interactions with the anatomy might occur. For example, if the length D3 in the fully expanded condition is just slightly smaller than the boundaries of the ventricular tissue, and the length D3 temporarily increased during delivery, the ventricular anchor 204 might undesirably interact with tissue during expansion, which could result in undesired positioning. By limiting the length D3 during deployment, this potential problem may be avoided.

In addition to preventing premature engagement of the ventricular anchor 204 with the native tissue, a reduction in length D3 may also affect the angle at which the barbs 208 approach the native tissue. Referring again to FIG. 3, during deployment, in the absence of constraining members 400, the barbs 208 may be angled to point substantially vertically toward the atrial or inflow end of the prosthetic heart valve. If the barbs 208 engage the native tissue when in this orientation, it may be suboptimal. For example, if the barbs 208 engage the native tissue in the orientation shown in FIG. 3, as the atrial end of the prosthetic heart valve 200 is released from the overlying sheath of the delivery device DD, the barbs 208 may hinge further above horizontal (represented by angle β in FIG. 3). This hinging motion of the barbs 208 may not be preferable for ideal engagement with the native tissue or myocardium. However, by including constraining members 400, the lengths D5 and D3 may be limited. Thus, the tendency for the ventricular anchor 204 (and particular the barbs 208) to hinge after the remainder of the prosthetic heart valve 200 is deployed form the delivery device DD, may be limited or eliminated. The limitation of the length D5 and the associated angle may be particularly helpful in improving the engagement angle of the barbs 208 with the native tissue.

Still further, another result of the constraining members 400 is to increase length D4. Referring again to FIG. 3, length D4 may generally refer to the length of the central waist portion 203 of the outer frame 201. In prior art prosthetic heart valves, such as prosthetic heart valve 100 that lacks constraining members 400, the deployment method typically includes allowing the ventricular anchors 104 to expand within the ventricle, and then translating (or pulling) the prosthetic heart valve proximally. In other words, while the ventricular anchors 104 are expanded, but while the atrial end of the prosthetic heart valve remains collapsed within the overlying sheath of the delivery device, the ventricular anchors 104 are pulled into engagement with the native tissue. After the ventricular anchors 104 are engaged with the native tissue, only then are the atrial anchors 102 of the prosthetic heart valve 100 released form the delivery device. This sequence is typically required in the prior art prosthetic heart valve 100 in order to land the central waist portion 103 in the plane of the native valve annulus. However, it may be preferable to reduce or eliminate the amount of translation needed to land the central waist portion 103 within the native valve annulus. Part of the reason why the axial translation may be necessary in the prior art prosthetic heart valve 100 is because of the tendency for the ventricular anchor 104 to axially foreshorten as it expands radially. In other words, if the outer frame 101 were fully cylindrical in the expanded condition (in which case length D4 would be a maximum), the outer frame would be easily aligned within the plane of the native valve annulus without the "waist" portion moving axially. However, referring again to FIGS. 3 and 5A, the constraining members 400 may act to limit length D5, and thus also act to limit length D4. As a result of this, when the prosthetic heart valve 200 is released from the overlying sheath of the delivery device DD, the central waist 203 of the outer frame 201 could be aligned with the plane of the native valve annulus while the ventricular anchors 204 are deployed. This configuration may thus reduce or eliminate the need to axially translate the prosthetic heart valve 200 mid-deployment, which may in turn increase the accuracy and repeatability of the deployment procedure.

It should be understood from the above that constraining member 300 and constraining members 400 may be used together or separately to provide the benefits described above. In other words, constraining member 300 may help limit motion that might otherwise damage the prosthetic heart valve leaflets L, while constraining members 400 may help reduce the likelihood of damaging native tissue during deployment, while also allowing for a more accurate and more repeatable deployment of the prosthetic heart valve within the desired position and orientation in the native heart valve annulus.

Figure 5B:
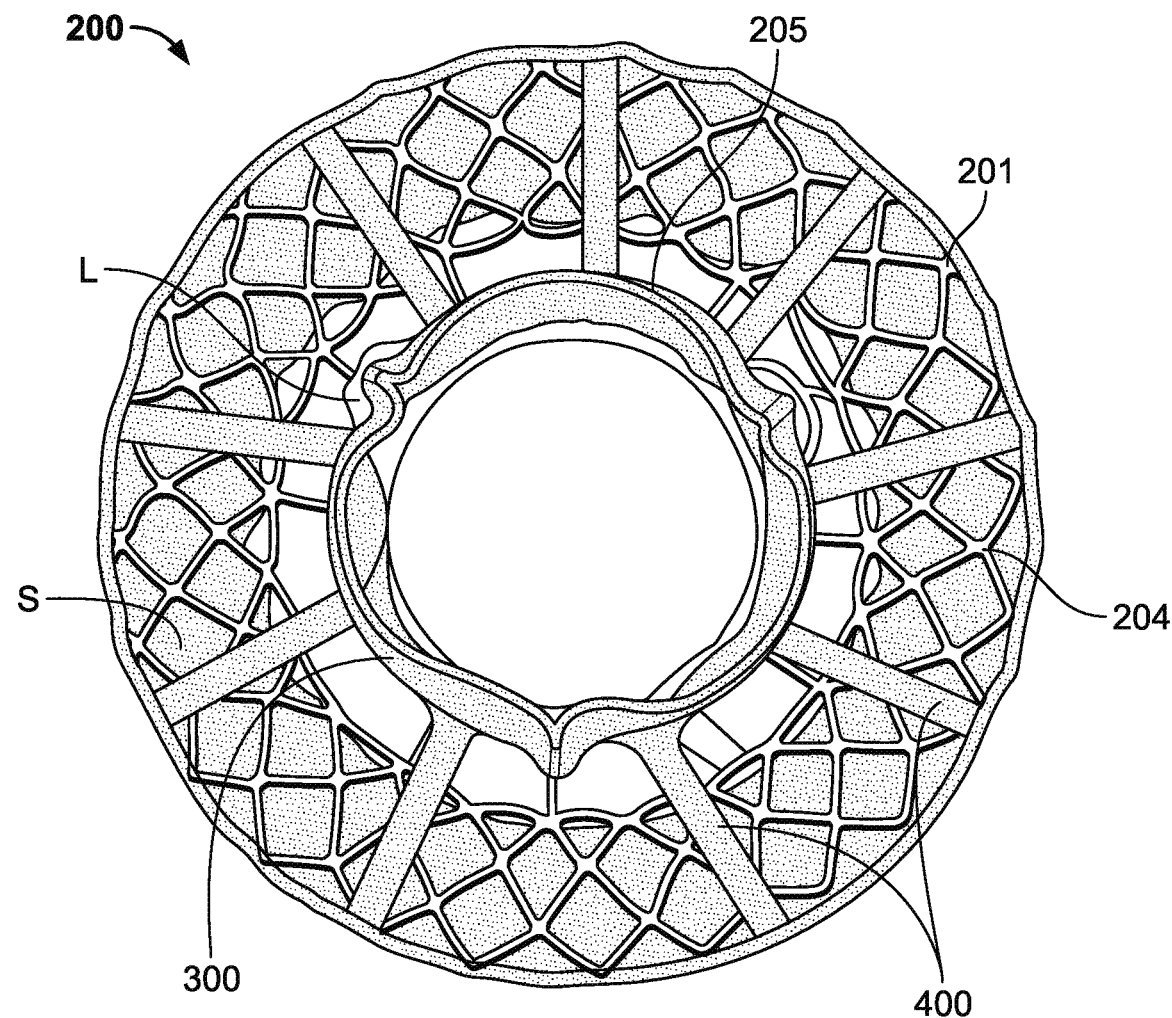

FIG. 5B is a bottom view of prosthetic heart valve 200, looking at the outflow end of the prosthetic valve, including both constraining member 300 and constraining members 400 formed as a single member, which may be an inelastic member. FIG. 5B illustrates the prosthetic leaflets L and skirt S coupled to the valve, with the constraining members 400 formed as a plurality of individual strips formed as extensions of constraining member 300. Although FIG. 5B illustrates nine individual constraining members 400, it should be understood that more or fewer may be appropriate. The length of the constraining members 400 may be equal to length D5 shown in FIG. 3.

Figure 6A:
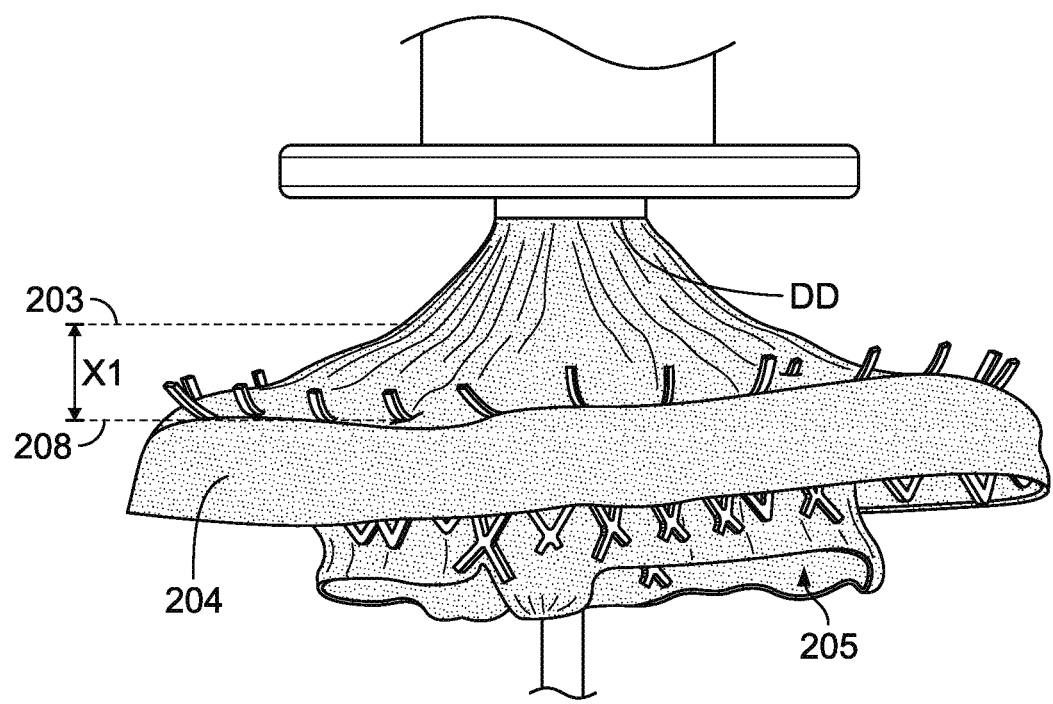
FIGS. 6A-B illustrate a prosthetic heart valve with and without constraining features, respectively, mid-deployment from a delivery device.
Figure 6B:
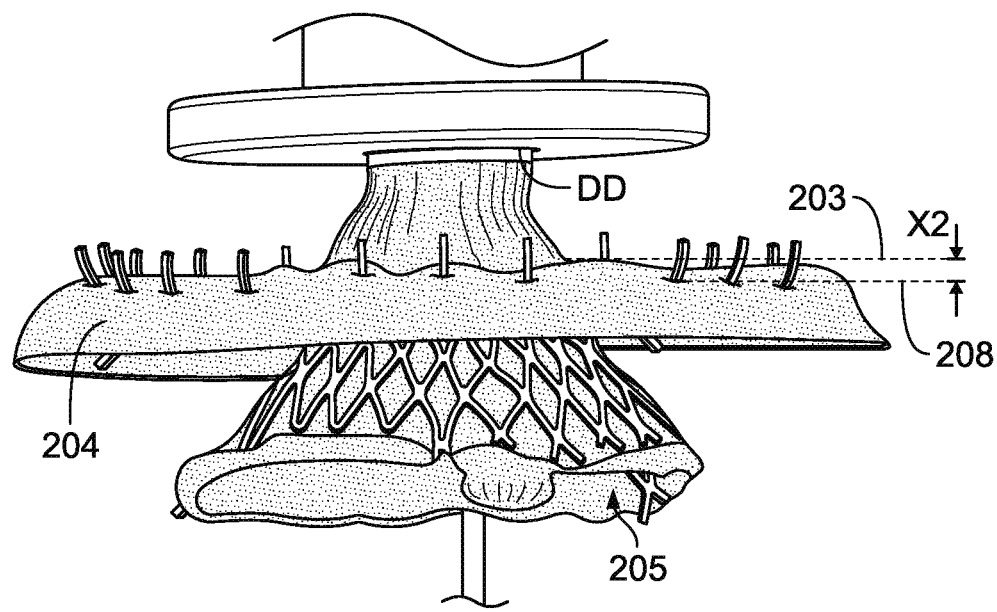

At least some of the concepts described above are further illustrated in FIGS. 6A-B. FIGS. 6A-B both illustrate prosthetic heart valve 200 being expressed from an overlying sheath of a delivery device DD with the ventricular anchor 204 released but the atrial anchor still maintained in a collapsed condition by the delivery device. However, the prosthetic heart valve 200 of FIG. 6A includes constraining members 300, 400 in the configuration illustrated in FIG. 5B, whereas the prosthetic heart valve 200 of FIG. 6B lacks constraining members 300 and 400. Without constraining features 400, as best illustrated in FIG. 6B, as the prosthetic heart valve 200 is released from the delivery device DD, the distance X2 between the level of the central waist portion 203 and the barbs 208 is very small. In this configuration, the delivery DD will likely need to be moved proximally (toward the atrium) during the final release of the prosthetic heart valve 200, because at the illustrated level of deployment, the barbs 208 have engaged with the native tissue, but the user still has to move the delivery device proximally to locate the central waist portion 203 of the prosthetic valve at the annulus of the native valve. However, in FIG. 6A, constraining members 400 may result in the distance X1 between the central waist portion 203 and the barbs 208 being increased to more closely correspond to the expected distance between the waist portion and the barbs when the prosthetic heart valve is fully implanted. Thus, constraining features 400 alter the way in which the ventricular portion 204 deploys relative to the central waist portion 203 so that the delivery device DD needs not (or need only minimally) move proximally toward the atrium to complete the final valve release to locate the central waist portion 203 in the native valve annulus.

According to a first aspect of the disclosure, a prosthetic heart valve comprises:

a collapsible and expandable outer frame configured to engage tissue of a native heart valve, the outer frame having an atrial portion adapted to be positioned on an atrial side of the native heart valve, a ventricle portion adapted to be positioned on a ventricle side of the native heart valve, and a narrowed waist portion between the atrial portion and the ventricle portion;

a collapsible and expandable inner frame positioned radially inward of the outer frame and coupled to the outer frame, a constraining band extending around a circumference of the inner frame; and a prosthetic valve assembly coupled to, and positioned radially inward of, the inner frame; and/or the inner frame has a first diameter in the absence of applied forces, the constraining band configured to limit the inner frame from expanding to a second diameter greater than the first diameter; and/or the constraining band extends around an exterior of the inner frame; and/or the constraining band is formed of a woven fabric; and/or the woven fabric is polyethylene terephthalate ("PET"); and/or the constraining band is positioned at an outflow end of the inner frame; and/or the prosthetic valve assembly includes a plurality of prosthetic leaflets having first ends attached to the inner frame and second free ends, the second free ends configured to coapt with each other to provide unidirectional flow of blood through the prosthetic heart valve, the second free ends being axially aligned with the constraining band; and/or at least one constraining member having a first end coupled to the inner frame and a second end coupled to the outer frame; and/or the at least one constraining member includes a plurality of constraining members spaced apart from one another in a circumferential direction of the inner frame; and/or the plurality of constraining members are formed integrally with the constraining band; and/or the plurality of constraining members are formed separately from the constraining band, each of the plurality of constraining members being fixed to the constraining band; and/or the plurality of constraining members are wires formed of metal or metal alloys; and/or the plurality of constraining members are wires formed of nitinol; and/or the constraining band and the constraining members are all formed of a woven synthetic fabric; and/or the synthetic fabric is PET; and/or the at least one constraining member includes a single constraining member having a circular shape, the single constraining member being coupled to the outer frame at spaced apart locations in a circumferential direction of the single constraining member.

According to another aspect of the disclosure, a method of implanting a prosthetic heart valve into a native heart valve annulus comprises:

delivering the prosthetic heart valve to a location at or adjacent the native heart valve annulus while the prosthetic heart valve is maintained in a collapsed condition within an overlying sheath of a delivery device, the prosthetic heart valve including a collapsible and expandable outer frame, a collapsible and expandable inner frame positioned radially inward of the outer frame and coupled to the outer frame, a prosthetic valve assembly coupled to, and positioned radially inward of, the inner frame, and a constraining band extending around a circumference of the inner frame;

deploying an outflow end of the prosthetic heart valve from the delivery device; and deploying an inflow end of the prosthetic heart valve from the delivery device after deploying the outflow end of the prosthetic heart valve, so that the inner frame has a first diameter after deployment of the inflow end of the prosthetic heart valve;

wherein the constraining band prevents the inner frame from expanding to a second diameter larger than the first diameter during deployment of the outflow end of the prosthetic heart valve; and/or the constraining band is formed of woven PET; and/or the prosthetic heart valve further includes at least one constraining member having a first end coupled to the inner frame and a second end coupled to the outer frame; and/or during deployment of the outflow end of the prosthetic heart valve, a distance between the inner frame and the outer frame is limited to a length of the at least one constraining member.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve comprising:
a collapsible and self-expandable outer frame configured to engage tissue of a native heart valve, the outer frame having an atrial portion adapted to be positioned on an atrial side of the native heart valve, a ventricle portion adapted to be positioned on a ventricle side of the native heart valve, and a narrowed waist portion between the atrial portion and the ventricle portion;
a collapsible and self-expandable inner frame having an inflow end and an outflow end and being fixedly coupled to the outer frame by a plurality of coupling members so that, prior to expression of the prosthetic heart valve from a delivery device, the inner frame is positioned radially inward of the outer frame, and a constraining band directly coupled to the inner frame and extending around a circumference of the inner frame, wherein the constraining band is positioned at the outflow end of the inner frame; and
a prosthetic valve assembly coupled to, and positioned radially inward of, the inner frame and being configured to allow unidirectional flow of blood through the prosthetic valve assembly from the inflow end to the outflow end, the prosthetic valve assembly including a plurality of prosthetic leaflets having first ends attached to the inner frame and second free ends, the second free ends configured to coapt with each other to provide the unidirectional flow of blood through the prosthetic heart valve,
wherein the inner frame has a first diameter in the absence of applied forces, the constraining band configured to limit the inner frame from expanding to a second diameter greater than the first diameter, wherein limiting the inner frame from expanding to the second diameter greater than the first diameter during expression of the prosthetic heart valve from a delivery device limits stretching of the plurality of prosthetic leaflets,
wherein the outer frame includes a first plurality of coupling arms, and the inner frame includes a second plurality of coupling arms, wherein the first plurality of coupling arms are coupled to the second plurality of coupling arms, prior to expression of the prosthetic heart valve from a delivery device, via the plurality of coupling members,
wherein, in an expanded condition of the prosthetic heart valve, the first plurality of coupling arms extend radially inward toward the second plurality of coupling arms and the second plurality of coupling arms extend radially outward toward the first plurality of coupling arms.

2. The prosthetic heart valve of claim 1, wherein the constraining band extends around an exterior of the inner frame.

3. The prosthetic heart valve of claim 1, wherein the constraining band is formed of a woven fabric.

4. The prosthetic heart valve of claim 3, wherein the woven fabric is polyethylene terephthalate ("PET").

5. The prosthetic heart valve of claim 1, wherein the second free ends of the plurality of prosthetic leaflets are axially aligned with the constraining band.

6. The prosthetic heart valve of claim 1, further comprising at least one constraining member having a first end coupled to the inner frame and a second end coupled to the outer frame.

7. The prosthetic heart valve of claim 6, wherein the at least one constraining member includes a plurality of constraining members spaced apart from one another in a circumferential direction of the inner frame.

8. The prosthetic heart valve of claim 7, wherein the plurality of constraining members are formed integrally with the constraining band.

9. The prosthetic heart valve of claim 7, wherein the plurality of constraining members are formed separately from the constraining band, each of the plurality of constraining members being fixed to the constraining band.

10. The prosthetic heart valve of claim 7, wherein the plurality of constraining members are wires formed of metal or metal alloys.

11. The prosthetic heart valve of claim 10, wherein the plurality of constraining members are wires formed of nitinol.

12. The prosthetic heart valve of claim 7, wherein the constraining band and the constraining members are all formed of a woven synthetic fabric.

13. The prosthetic heart valve of claim 12, wherein the synthetic fabric is PET.

14. The prosthetic heart valve of claim 1, wherein the constraining band is directly coupled to a ventricular end of the inner frame.

15. The prosthetic heart valve of claim 1, wherein the constraining band is directly coupled to and covers a terminal outflow end of the inner frame.

16. The prosthetic heart valve of claim 1, wherein the constraining band extends around an inner perimeter or an outer perimeter of the inner frame.

17. The prosthetic heart valve of claim 1, wherein the plurality of coupling members are rivets.

* * * * *